(12) United States Patent
Ledoussal et al.

(10) Patent No.: US 8,148,366 B2
(45) Date of Patent: Apr. 3, 2012

(54) SUBSTITUTED PYRAZOLO[3,4-E][DIAZEPIN-6-5(H)ONES AND ANALOGUES THEREOF, THEIR PREPARATION AND THEIR USE AS ANTIBACTERIAL MEDICAMENTS

(75) Inventors: Benoit Ledoussal, Romainville (FR);
Marie-Edith Gourdel, Romainville (FR); Emilie Renaud, Romainville (FR);
Camille Pierres, Romainville (FR);
Adel Kebsi, Romainville (FR)

(73) Assignee: Novexel SA, Romaninville (FR)

( * ) Notice: Subject to any disclaimer, the term of this patent is extended or adjusted under 35 U.S.C. 154(b) by 0 days.

(21) Appl. No.: 12/536,034

(22) Filed: Aug. 5, 2009

(65) Prior Publication Data

US 2010/0093784 A1     Apr. 15, 2010

(30) Foreign Application Priority Data

Oct. 10, 2008   (FR) ..................... 08 05602

(51) Int. Cl.
*A61K 31/55* (2006.01)
(52) U.S. Cl. ......... 514/221; 540/593; 544/359; 546/200
(58) Field of Classification Search .................. 514/221; 540/593; 544/359; 546/200
See application file for complete search history.

(56) References Cited

U.S. PATENT DOCUMENTS

| | | |
|---|---|---|
| 6,841,562 B2 | 1/2005 | Badque et al. |
| 7,148,322 B2 | 12/2006 | Boffelli et al. |
| 7,232,833 B2 | 6/2007 | Bigot et al. |
| 7,232,834 B2 | 6/2007 | Bacque et al. |
| 7,439,253 B2 | 10/2008 | Lampilas et al. |
| 2002/0049192 A1 | 4/2002 | Ledoussal et al. |
| 2002/0173501 A1 | 11/2002 | Ledoussal et al. |
| 2003/0008894 A1 | 1/2003 | Ledoussal et al. |
| 2003/0171587 A1 | 9/2003 | Ledoussal et al. |
| 2003/0207862 A1 | 11/2003 | Ledoussal et al. |
| 2004/0029882 A1 | 2/2004 | Ledoussal et al. |
| 2004/0038975 A1 | 2/2004 | Ledoussal et al. |
| 2005/0020572 A1 | 1/2005 | Aszodi et al. |
| 2005/0101589 A1 | 5/2005 | Ledoussal et al. |
| 2005/0245747 A1 | 11/2005 | Bacon et al. |
| 2006/0100436 A1 | 5/2006 | Ledoussal et al. |
| 2009/0018329 A1 | 1/2009 | Lampilas et al. |
| 2009/0062284 A1 | 3/2009 | Bacon et al. |
| 2009/0111851 A1 | 4/2009 | Ledoussal et al. |

FOREIGN PATENT DOCUMENTS

| | | |
|---|---|---|
| WO | WO/02/10172 | 2/2002 |
| WO | WO/02/100860 | 12/2002 |
| WO | WO/2004/022563 | 3/2004 |
| WO | WO/2004/052891 | 6/2004 |

*Primary Examiner* — James O Wilson
*Assistant Examiner* — Douglas M Willis

(57) ABSTRACT

The invention relates to nitrogenous heterocyclic compounds of formula (I):

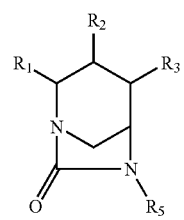

(I)

in which:
$R_1$ represents hydrogen, $-(CH_2)_m-NH_2$, $-(CH_2)_m-NH(C_1-C_6)$alk, $-(CH_2)_m-N(C_1-C_6)$alk$_2$, $-(CH_2)_m-NH-C(NH)NH_2$ or $-(CH_2)_m-NH-CH=NH$, m is equal to 1 or 2;
$R_2$ and $R_3$ together form a nitrogenous heterocycle of aromatic character with 5 vertices containing 1, 2 or 3 nitrogen atoms, substituted on a nitrogen atom by $R_4$;
$R_4$ represents hydrogen, $C_1-C_6$alk or a chain of formula:

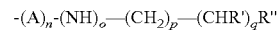

A represents C=O, C=NH or $SO_2$;
R' represents hydrogen or carboxy.

13 Claims, No Drawings

SUBSTITUTED PYRAZOLO[3,4-E][DIAZEPIN-6-5(H)ONES AND ANALOGUES THEREOF, THEIR PREPARATION AND THEIR USE AS ANTIBACTERIAL MEDICAMENTS

CROSS REFERENCE TO RELATED APPLICATIONS

This application claims priority to French Patent Application No. 08 05 602, filed Oct. 10, 2008, which is incorporated by reference herein.

BACKGROUND AND SUMMARY

The invention relates to nitrogenous heterocyclic compounds, their preparation and their use as antibacterial medicaments.

The applications WO 02/010172, 02/100860, 04/022563 and 04/052891 describe polycyclic compounds which are useful in combating pathogenic bacteria. The Applicant has discovered novel related compounds, possessing remarkable and completely unexpected antibacterial properties. These compounds possess more particularly an excellent activity on *Pseudomonas aeruginosa*, a bacterial strain frequently encountered in nosocomial infections as well as in patients suffering from mucoviscidosis. This useful and unexpected activity is not present in the compounds of the applications cited above. It is illustrated hereafter in the experimental part.

Moreover, the compounds of the invention have been shown to be active on animal infection models, including on strains which are usually resistant to the commonly used antibiotics. The compounds of the invention are capable of counteracting the main resistance mechanisms of the bacteria which are the β-lactamases, efflux pumps and porin mutations.

The compounds of the invention correspond to formula (I), in their possible isomeric or diasteroisomeric forms, or mixtures:

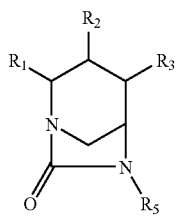

(I)

in which:

$R_1$ represents a hydrogen atom or a $-(CH_2)_m-NH_2$; $-(CH_2)_m-NH(C_1-C_6)$alk, $-(CH_2)_m-N(C_1-C_6)$alk$_2$, $-(CH_2)_m-NH-C(NH)NH_2$ or $-(CH_2)_m-NH-CH=NH$ radical, in which m is equal to 1 or 2;

$R_2$ and $R_3$ together form a nitrogenous heterocycle of aromatic character with 5 vertices containing 1, 2 or 3 nitrogen atoms, substituted on a nitrogen atom by $R_4$;

$R_4$ represents a hydrogen atom, a $(C_1-C_6)$alk radical or a chain of formula:

A represents a C=O, C=NH or $SO_2$ group;
R' represents a hydrogen atom or a carboxy group;
R" represents a hydrogen atom or an $NH_2$, $NH(C_1-C_6)$alk, $N(C_1-C_6)$alk$_2$, $CONH_2$, $CONH(C_1-C_6)$alk, $CON(C_1-C_6)$alk$_2$ group, or a saturated heterocycle with 5 or 6 vertices containing 1 or 2 nitrogen atoms and, if appropriate, another heteroatom chosen from oxygen and sulphur, fixed to the chain by a nitrogen atom or by a carbon atom and optionally substituted by a $(C_1-C_6)$alk radical;

n, o and q represent 0 or 1 and p represents an integer from 0 to 4;

$R_5$ represents an $OSO_3H$ or $OCHFCO_2H$ or $OCF_2CO_2H$ group;

it being understood that:
$R_1$ is different from hydrogen, $-(CH_2)_m-NH_2$, $-(CH_2)_m-NH(C_1-C_6)$alk or $-(CH_2)_m-N(C_1-C_6)$alk$_2$ when $R_4$ is hydrogen, $-(C_1-C_6)$alk, $-(C=O)_n-(CH_2)_{(0-5)}-NH_2$, $-(C=O)_n-(CH_2)_{(0-5)}-NH(C_1-C_6)$alk or $-(C=O)_n-(CH_2)_{(0-5)}-N(C_1-C_6)$alk$_2$ and $R_5$ is an $OSO_3H$ group, or when $R_4$ has all of the values of R" above except for the heterocycle as defined above,
and n, o, p and q cannot all be equal to 0 except when R" is hydrogen or a $CONH_2$, $CONH(C_1-C_6)$alk, $CON(C_1-C_6)$alk$_2$ group, or a heterocycle;

in the free form and in the form of zwitterions and salts with pharmaceutically acceptable bases and mineral or organic acids.

By $(C_1-C_6)$ alkyl radical is meant in particular the methyl, ethyl, propyl or isopropyl radical, as well as linear or branched butyl, pentyl or hexyl;

By heterocycle of aromatic character with 5 vertices containing 1, 2 or 3 nitrogen atoms, is meant those chosen from the list which follows, the two bonds symbolizing the nitrogen-ring junction formed by $R_2$ and $R_3$:

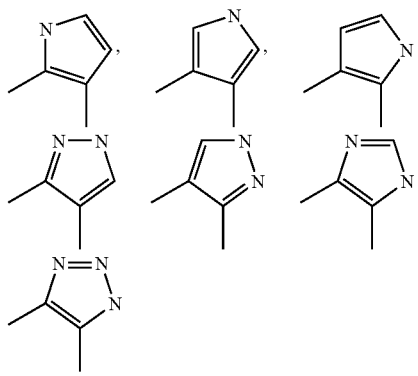

By saturated heterocycle with 5 or 6 vertices containing 1 or 2 nitrogen atoms and, if appropriate, an oxygen or sulphur atom, is meant in particular a ring with 5 vertices of pyrrolidine, imidazolidine or pyrazolidine type, or a ring with 6 vertices of piperidine, piperazine, morpholine or thiomorpholine type, the heterocycle being linked to the chain by a nitrogen atom or by a carbon atom.

Among the acid salts of the products of formula (I), there may be mentioned, among others, those formed with the mineral acids, such as hydrochloric, hydrobromic, hydroiodic, sulphuric or phosphoric acid or with organic acids such as formic, acetic, trifluoroacetic, propionic, benzoic, maleic, fumaric, succinic, tartaric, citric, oxalic, glyoxylic, aspartic, alkanesulphonic acids, such as methanesulphonic and ethanesulphonic acids, arylsuiphonic acids such as benzenesulphonic and paratoluenesulphonic acids. Among the salts of the bases of the products of formula (I) there may be mentioned, among others, those formed with mineral bases such as, for example, sodium, potassium, lithium, calcium, magnesium or ammonium hydroxide or organic bases such as, for example, methylamine, propylamine, trimethylamine, diethylamine, triethylamine, N,N-dimethylethanolamine, tris (hydroxymethyl)aminomethane, ethanolamine, pyridine, picoline, dicyclohexylamine, morpholine, benzylamine, procaine, lysine, arginine, histidine, N-methylglucamine, or also the salts of phosphonium, such as alkylphosphonium, arylphosphoniums, alkylarylphosphonium, alkenylaryiphosphonium or the salts of quaternary ammoniums such as tetra n-butylammonium salt.

The asymmetrical carbon atoms contained in the compounds of formula (I) can independently of one another have the R, S or RS configuration and the compounds of formula (I) are therefore presented in the form of pure enantiomers or pure diastereoisomers or in the form of a mixture of enantiomers in particular of racemates, or mixtures of diastereoisomers. Moreover, the $R_1$ substituent on the one hand and the —C(O)—$NR_5$— chain on the other hand being able to be in cis and/or trans position with respect to the ring to which they are fixed, the compounds of formula (I) are presented in the form of cis isomers or trans isomers or mixtures. Among the compounds of formula (I) as defined above, a subject of the invention is in particular the compounds in which $R_2$ and $R_3$ together form a pyrazolyl heterocycle.

Among the compounds of formula (I) as defined previously, a subject of the invention is in particular those in which $R_1$ represents a —$(CH_2)_m$—$NH_2$ radical, as well as those in which $R_1$ represents a —$(CH_2)_m$—NH—C(NH)$NH_2$ radical, m in either case being equal to 1. Among the compounds of formula (I), a subject of the invention is also in particular those in which $R_4$ represents a chain of formula $-(A)_n-(NH)_o$—$(CH_2)_p$—$(CHR')_q$ R"as defined previously, and quite particularly those in which $R_4$ represents a chain of formula —C(O)—NH—$(CH_2)_p$—$(CHR')_q$ R" in which R', R", p and q are as defined above. Among the compounds of formula (I), a subject of the invention is also in particular those in which $R_4$ represents a hydrogen atom or a ($C_1$-$C_6$)alk radical and $R_1$ represents a —$CH_2)_m$—NH—C(NH)$NH_2$ or —$(CH_2)_m$—NH—CH=NH radical, in which m is equal to 1.

Among the compounds of formula (I), a subject of the invention is in particular the compounds described hereafter in the experimental part, in particular those whose names follow:

trans 8-(aminomethyl)-2-(2-amino-ethyl-carbamoyl)-4,8-dihydro-5-(sulphooxy)-4,7-methano-7H-pyrazolo[3,4-e] [1,3] diazepin-6(5H)-one, trans 8-(aminomethyl)-2-(4-piperazine-1-carbonyl)-4,8-dihydro-5-(sulphooxy)-4,7-methano-7H-pyrazolo[3,4-e] [1,3] diazepin-6(5H)-one, trans 8-(aminomethyl)-4,8-dihydro-2-(2-dimethylamino-ethyl-carbamoyl)-5-(sulphooxy)-4,7-methano-7H -pyrazolo[3,4-e] [1,3] diazepin-6(5H)-one, trans 8-(aminomethyl)-2-(3-amino-propyl-carbamoyl)-4,8-dihydro-5-(sulphooxy)-4,7-methano-7H -pyrazolo[3,4-e] [1,3] diazepin-6(5H)-one, trans 8-(aminomethyl)-2-(carbamoyl-methyl-carbamoyl)-4,8-dihydro-5-(sulphooxy)-4,7-methano-7H-pyrazolo [3,4-e] [1,3] diazepin-6(5H)-one, trans 8-(aminomethyl)-1-(carbamimidoyl)-4,8-dihydro-5-(sulphooxy)-4,7-methano-7H-pyrazolo[3,4-e] [1,3] diazepin-6(5H)-one, trans 8-(aminomethyl)-2-(carbamimidoyl)-4,8-dihydro-5-(sulphooxy)-4,7-methano-7H-pyrazolo[3,4-e] [1,3] diazepin-6(5H)-one 8, trans 8-(amino-methyl)-4,8-dihydro-2-(piperidine-4-carbonyl)-5-(sulphooxy)-4,7-methano-7H-pyrazolo[3,4-e] [1,3] diazepin-6(5H)-one, trans 8-(amino-methyl)-2-(3-amino-3-carboxy-propyl)-4,8-dihydro-5-(sulphooxy)-4,7-methano-7H-pyrazolo[3,4-e] [1,3] diazepin-6(5H)-one, trans 8-(guanidino-methyl)-4,8-dihydro-5-(sulphooxy)-4,7-methano-7H-pyrazolo[3,4-e] [1,3] diazepin-6(5H)-one, trans 8-(guanidino-methyl)-4,8-dihydro-1-methyl-5-(sulphooxy)-4,7-methano-7H-pyrazolo[3,4-e] [1,3] diazepin-6(5H)-one, trans 8-(guanidino-methyl)-2-carbamoyl-4,8-dihydro-(sulphooxy)-4,7-methano-7H-pyrazolo[3,4-e] [1,3] diazepin-6(5H)-one, trans 8-(amino-methyl)-4,8-dihydro-1-methyl-5-(carboxy-difluoro-methoxy)-4,7-methano-7H-pyrazolo[3,4-e] [1,3] diazepin-6(5H)-one, trans 8-(amino-methyl)-2-(amino-carbamoyl)-4,8-dihydro-5-(sulphooxy)-4,7-methano-7H-pyrazolo[3,4-e] [1,3] diazepin-6(5H)-one, in the free form, in the form of zwittterions and salts with pharmaceutically acceptable bases and mineral or organic acids, and in their possible isomeric or diastereoisomeric forms, or mixtures.

Another subject of the invention is a process for the preparation of the compounds of formula (I), characterized in that a compound of formula (II):

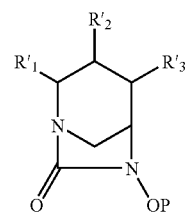

(II)

in which $R'_1$, represents an $R_1$ radical in which, if appropriate, the amino function or functions present are protected, $R'_2$ and $R'_3$ together form a nitrogenous heterocycle of aromatic character with 5 vertices containing 1, 2 or 3 nitrogen atoms and P represents a protective group of the hydroxy radical, is treated in the presence of a base, by diphosgene, then by an amine of formula (III):

H—NH—$(CH_2)_p$—$(CHR'_a)_q$R''' (III)

in which $R'_a$ and R''' represent respectively R' and R" in which, if appropriate, the reactive carboxy and amino functions are protected, and p and q are as defined above, in order to obtain a compound of formula (IV):

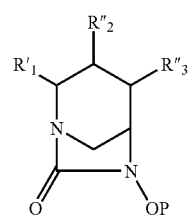

(IV)

in which $R'_1$ and $_p$ are as defined above and $R''_2$ and $R''_3$ together form a nitrogenous heterocycle of aromatic character with 5 vertices containing 1, 2 or 3 nitrogen atoms, substituted on a nitrogen atom by a chain of formula —C(O)—NH—$(CH_2)_p$—$(CHR'_a)_q$ R''' in which $R'_a$, R''', $p$ and q are as defined above, then the radical hydroxy is deprotected and the compound obtained subjected to a sulphation reaction by the action of complexed $SO_3$, or to the action of a reagent of formula Hal-CHF—$CO_2$alk or of formula Hal-$CF_2$—$CO_2$alk, in which Hal represents a halogen atom different from fluorine and alk represents an alkoyl radical containing 1 to 6 carbon atoms, in the presence of a base, then to hydrolysis of the alkoyl ester obtained, then, if appropriate, the compound obtained is subjected to one or more of the following reactions, in an appropriate order:
  deprotection of the amine and, if appropriate, carboxy function or functions present,
  salification,
  ion exchange,
  resolution or separation of diastereoisomers.

Another subject of the invention is a process for the preparation of compounds of formula (I), characterized in that a compound of formula (II) as defined above is treated with a base, then with a reagent of formula (V):

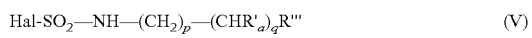

Hal-$SO_2$—NH—$(CH_2)_p$—$(CHR'_a)_q$R'''    (V)

in which Hal represents a halogen atom and $R'_a$, R''', p and q are as defined above, in order to obtain a compound of formula (IVa):

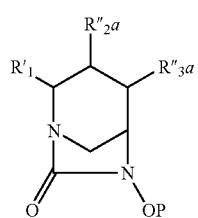

(IVa)

in which $R'_1$, and P are as defined above and $R''_{2a}$ and $R''_{3a}$ together form a nitrogenous heterocycle of aromatic character with 5 vertices containing 1, 2 or 3 nitrogen atoms, substituted on a nitrogen atom by a chain of formula —$SO_2$—NH—$(CH_2)_p$—$(CHR'_a)_q$ R''' in which $R'_a$, R''', p and q are as defined above, then the hydroxy radical is deprotected and the synthesis continued as described above.

Another subject of the invention is a process for the preparation of compounds of formula (I), characterized in that a compound of formula (II) as defined above is treated, if appropriate in the presence of a base, with a reagent of formula (VI):

B—C(O)—$(NH)_o$—$(CH_2)_p$—$(CHR'_a)_q$R'''    (VI)

in which B represents an OH radical or a halogen atom and $R'_a$, R''', o, p and q are as defined above, in order to obtain a compound of formula (IVb):

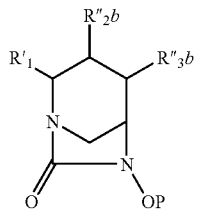

(IVb)

in which $R'_1$ and P are as defined above and $R''_{2b}$ and $R''_{3b}$ together form a nitrogenous heterocycle of aromatic character with 5 vertices containing 1, 2 or 3 nitrogen atoms, substituted on a nitrogen atom by a chain of formula —C(O)—$(NH)_o$—$(CH_2)_p$—$(CHR'_a)_q$ R''' in which $R'_a$, R''', o, p and q are as defined above, then the synthesis as described above is continued.

Another subject of the invention is a process for the preparation of compounds of formula (I), characterized in that a compound of formula (II) as defined above, is treated in the presence of a base, with a reagent of formula (VII):

S=C(NHP')$_2$    (VII)

in which P' represents a protective group of the amino function, in order to obtain a compound of formula (IVc):

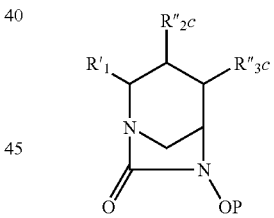

(IVc)

in which $R'_1$ and P are as defined above and $R''_{2c}$ et $R''_{3c}$ together form a nitrogenous heterocycle of aromatic character with 5 vertices containing 1, 2 or 3 nitrogen atoms, substituted on a nitrogen atom by a chain of formula —C(=NH)—NHP' in which P' is as defined above, then the synthesis as described above is continued.

Another subject of the invention is a process for the preparation of compounds of formula (I), characterized in that a compound of formula (II) as defined above is treated by a reagent of formula (VIII):

O=C=N—$(CH_2)_p$—$(CHR'_a)_q$R'''    (VIII)

in which R'$_a$, R''', p and q are as defined above, in order to obtain a compound of formula (IVd)

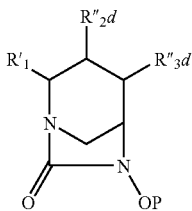

in which R'$_1$ and P are as defined above and R''$_{2d}$ and R''$_{3d}$ together form a nitrogenous heterocycle of aromatic character with 5 vertices containing 1, 2 or 3 nitrogen atoms, substituted on a nitrogen atom by a chain of formula —(CO)—NH—(CH$_2$)$_p$—(CHR'$_a$)$_q$ R''' in which R'$_a$, R''', p and q are as defined above, then the synthesis as described above is continued.

A compound of formula (I) in which R$_4$ represents a CO—NH$_2$ or CO—NH(C$_1$-C$_6$)alk group can also be obtained by the action of the compound of formula (II) as defined above, with trimethylsilyl isocyanate or with an isocyanate of formula (C$_1$-C$_6$)alk-N=C=O, in order to obtain a corresponding compound of formula (IV), the synthesis as described above is continued.

Another subject of the invention is a process for the preparation of compounds of formula (I) characterized in that a compound of formula (II):

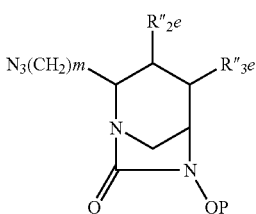

in which R''$_{2e}$ and R''$_{3e}$ together form a nitrogenous heterocycle of aromatic character with 5 vertices containing 1, 2 or 3 nitrogen atoms optionally substituted by a (C$_1$-C$_6$)alk radical and P is as defined above, is treated by a reagent of formula (IX):

CH$_3$—S—C(=NP')NHP'     (IX)

in which P' is as defined above, in order to obtain a compound of formula (X):

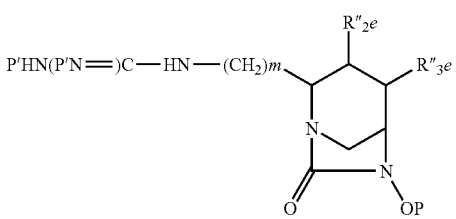

in which R''$_{2e}$, R''$_{3e}$, m, P and P' are as defined above. then the synthesis as described above is continued.

Prior protection of the amine function at R'$_1$ and in the reagents of formulae III, V, VI, VII, VIII et IX is in particular carried out in the form of benzylated or tritylated derivatives, in the form of carbamates, in particular allyl, benzyl, phenyl or tertbutyl, or also in the form of silylated derivatives such as tertbutyl, dimethyl, trimethyl, triphenyl or also diphenyltert-butyl-silyl, or also phenylsulphonylalkyl or cyanoalkyl derivatives. The deprotection can be carried out by different methods known to a person skilled in the art, depending on the nature of the protective group. It can in particular be carried out by the action of an acid, for example trifluoroacetic acid, the deprotected compound then being obtained in the form of the acid salt. It can also be carried out by hydrogenolysis or using soluble Palladium O complexes or by the action of tetrabutylammonium fluoride or by reduction. An illustration is provided hereafter in the experimental part.

The prior protection of the carboxy at R'a in the reagents of formulae III, V, VI and VIII is in particular carried out in the form of ester type derivatives, in particular alkyl, allyl, benzyl, benzhydryl or p-nitro benzyl. The deprotection can be carried out by different methods known to a person skilled in the art, for example by saponification, acid hydrolysis, hydrogenolysis or cleavage using soluble Palladium O complexes.

The prior protection of the hydroxy of the compound of formula (II) is carried out in a standard fashion, in the form of ethers, esters or carbonates. The ethers can be alkyl or alkoxyalkyl ethers, preferably methyl or methoxyethoxymethyl ethers, aryl or preferably aralkyl ethers, for example benzyl, or silylated ethers, for example the silylated derivatives mentioned above. The esters can be any cleavable ester known to a person skilled in the art and preferably the acetate, propionate or benzoate or p-nitrobenzoate. The carbonates can be for example methyl, tertbutyl, allyl, benzyl or p-nitrobenzyl carbonates The deprotection is carried out by the means known to a person skilled in the art, in particular saponification, hydrogenolysis, cleavage by soluble Palladium O complexes, hydrolysis in acid medium or also, for the silylated derivatives, treatment with tetrabutylammonium fluoride. Illustrations of the above protections and deprotections are provided hereafter in the experimental part.

The base in the presence of which the compound of formula (II) is reacted and the diphosgene can for example be an amine such as triethylamine, but other bases known to a person skilled in the art for reactions of this type can be used. It is possible to operate in a solvent such as methylene chloride. The sulphation reaction is carried out by the action of SO$_3$ complexes such as SO$_3$-pyridine or SO$_3$-dimethylformamide, by operating in pyridine or in dimethylformamide, the salt formed, for example the pyridine salt, then being able to be exchanged for example for a salt of another amine, quaternary ammonium or alkali metal. An illustration is provided in the experimental part.

The salification by acids is if appropriate carried out by adding an acid in soluble phase to the compound. The salification by bases of the sulphooxy function can be carried out from the salt of the amine and in particular pyridine obtained during the action of the SO$_3$-amine complex and the other salts are obtained from this amine salt. It is possible in particular to operate by ion exchange resin. The separation of the enantiomers and diastereoisomers can be carried out according to the techniques known to a person skilled in the art, in particular, chiral or non-chiral phase chromatography. Examples of conditions which can be used are also described in the application WO 04/052891 or also in the application WO 02/100860. The base in the presence of which the compound of formula (II) is reacted prior to the action of the reagent of formula (V) can for example be an alkaline hydride such as sodium hydride, but other bases known to a person skilled in the art for reactions of this type can be used. The reaction can be carried out in tetrahydrofuran. The base in the presence of which the compound of formula (II) is reacted with the reagent of formula (VI) in which B represents a halogen can for example be an amine such as diisopropylethylamine or triethylamine. The operation can be carried out in dimethylformamide or dichloromethane.

The conditions under which the compound of formula (II) is reacted with the reagent of formula (VI) in which B represents an OH, are the standard conditions for peptide couplings known to a person skilled in the art. Such conditions are illustrated hereafter in the experimental part. The base in the presence of which the compound of formula (II) and the reagent of formula (VII) are reacted can for example be an amine such as triethylamine, but other bases known to a person skilled in the art for reactions of this type can be used. The operation is carried out in the presence of mercury chloride and in a solvent such as methylene chloride.

The reaction of the compound of formula (II) with the reagent of formula (VIII) can be carried out in acetonitrile or a mixture with tetrahydrofuran. The reaction of the compound of formula (II') with the reagent of formula (IX) is carried out in the presence of trimethylphosphine and the operation is carried out for example in tetrahydrofuran or a tetrahydrofuran/toluene mixture. A subject of the invention is also the intermediate compounds of formulae (IV), (IVa), (IVb), (IVc), (IVd) and (X) as defined above. The compounds of formula (II) and (II') can be obtained by processes described in the applications WO 02/100860 or 04/052891.

As indicated above, the compounds of general formula (I) possess an excellent antibiotic activity on *Pseudomonas aeruginosa* as well as on animal infection models by strains resistant to the antibacterial agents commonly used. This remarkable and unexpected antibiotic activity had not been observed for the compounds described in the application WO 04/052891 and in particular for structurally similar compounds. This is illustrated hereafter.

These properties make said compounds, in the free form and in the form of zwitterions or pharmaceutically acceptable salts of acids and o bases, to be used as medicaments in the treatment of severe *Pseudomonas* infections, in particular nosocomial infections and, generally, major infections in patients at risk. They may in particular be infections of the airways, for example acute pneumonia or chronic infections of the lower airways, infections of the blood, for example the septicaemia, acute or chronic infections of the urinary tract, those of the auditory system, for example malignant external otitis, or chronic suppurative otitis, those of the skin and the soft tissues, for example dermatitis, infected wounds, folliculitis, pyodermatitis, resistant forms of acne, eye infections, for example corneal ulcer, those of the nervous system, in particular meningitis and cerebral abscess, cardiac infections such as endocarditis, bone and joint infections such as stenoarticular pyoarthrosis, vertebral osteomyelitis, pubic symphysitis, infections of the gastro-intestinal tract, such as necrotizing enterocolitis and perirectal infections.

A subject of the present invention is therefore also, as medicaments and in particular antibiotic medicaments, the compounds of formula (I) as defined above, in the free form and in the form of zwitterions and salts with pharmaceutically acceptable bases and mineral or organic acids. Among the compounds of formula (I), a subject of the invention is in particular, as medicaments, the compounds in which $R_2$ and $R_3$ together form a substituted pyrazolyl heterocycle. Among the compounds of formula (I), a more particular subject of the invention is, as medicaments, those in which $R_1$ represents a —$(CH_2)_m$—$NH_2$ radical, as well as those in which $R_1$ represents a —$(CH_2)_m$—NH—$C(NH)NH_2$ radical, m in either case being equal to 1. Among the compounds of formula (I), a subject of the invention is also in particular, as medicaments, those in which $R_4$ represents a chain of formula -$(A)_n$-$(NH)_o$—$(CH_2)_p$—$(CHR')_q$ R" as defined previously and quite particularly those in which $R_4$ represents a chain of formula —C(O)—NH—$(CH_2)_p$—$(CHR')_q$ R" in which R', R", p and q are as defined above. Among the compounds of formula (I), a subject of the invention is also in particular, as medicaments, those in which $R_4$ represents a hydrogen atom or a $(C_1-C_6)$alk radical and $R_1$ represents a —$(CH_2)_m$—NH—$C(NH)NH_2$ or —$(CH_2)_m$—NH—CH=NH radical, in which m is equal to 1.

Among the compounds of formula (I), a subject of the invention is quite particularly, as medicaments, the compounds described hereafter in the experimental part and in particular those the names of which follow:
- trans 8-(aminomethyl)-2-(2-amino-ethyl-carbamoyl)-4,8-dihydro-5-(sulphooxy)-4,7-methano-7H-pyrazolo[3,4-e] [1,3] diazepin-6(5H)-one,
- trans 8-(aminomethyl)-2-(4-piperazine-1-carbonyl)-4,8-dihydro-5-(sulphooxy)-4,7-methano-7H-pyrazolo[3,4-e] [1,3] diazepin-6(5H)-one,
- trans 8-(aminomethyl)-4,8-dihydro-2-(2-dimethylamino-ethyl-carbamoyl)-5-(sulphooxy)-4,7-methano-7H-pyrazolo[3,4-e] [1,3] diazepin-6(5H)-one,
- trans 8-(aminomethyl)-2-(3-amino-propyl-carbamoyl)-4,8-dihydro-5-(sulphooxy)-4,7-methano-7H-pyrazolo[3,4-e] [1,3] diazepin-6(5H)-one,
- trans 8-(aminomethyl)-2-(carbamoylmethyl-carbamoyl)-4,8-dihydro-5-(sulphooxy)-4,7-methano-7H-pyrazolo [3,4-e] [1,3] diazepin-6(5H)-one,
- trans 8-(aminomethyl)-1-(carbamimidoyl)-4,8-dihydro-5-(sulphooxy)-4,7-methano-7H-pyrazolo[3,4-e] [1,3] diazepin-6(5H)-one,
- trans 8-(aminomethyl)-2-(carbamimidoyl)-4,8-dihydro-5-(sulphooxy)-4,7-methano-7H-pyrazolo[3,4-e] [1,3] diazepin-6(5H)-one,
- trans 8-(amino-methyl)-4,8-di hydro-2-(piperidine-4-carbonyl)-5-(sulphooxy)-4,7-methano-7H-pyrazolo[3,4-e] [1,3] diazepin-6(5H)-one,
- trans 8-(amino-methyl)-2-(3-amino-3-carboxy-propyl)-4,8-dihydro-5-(sulphooxy)-4,7-methano-7H-pyrazolo[3,4-e] [1,3] diazepin-6(5H)-one,
- trans 8-(guanidino-methyl)-4,8-dihydro-5-(sulphooxy)-4,7-methano-7H-pyrazolo[3,4-e] [1,3] diazepin-6(5H)-one,
- trans 8-(guanidino-methyl)-4,8-dihydro-1-methyl-5-(sulphooxy)-4,7-methano-7H-pyrazolo[3,4-e] [1,3] diazepin-6(5H)-one,
- trans 8-(guanidino-methyl)-2-carbamoyl-4,8-dihydro-5-(sulphooxy)-4,7-methano-7H-pyrazolo[3,4-e] [1,3] diazepin-6(5H)-one,
- trans 8-(amino-methyl)-4,8-dihydro-1-methyl-5-(carboxy-difluoro-methoxy)-4,7-methano-7H-pyrazolo[3,4-e] [1,3] diazepin-6(5H)-one,
- trans 8-(amino-methyl)-2-(amino-carbamoyl)-4,8-dihydro-5-(sulphooxy)-4,7-methano-7H-pyrazolo[3,4-e] [1,3] diazepin-6(5H)-one, in the free form, in the form of zwittterions and salts with pharmaceutically acceptable bases and mineral or organic acids, in their possible isomeric or diasteroisomeric forms, or mixtures.

A subject of the invention is also the pharmaceutical compositions containing, as active ingredient, at least one of the compounds according to the invention as defined above.

These compositions can be administered by buccal, rectal, parenteral route, in particular intramuscular, or by local route as a topical application on the skin and mucous membranes. The compositions according to the invention can be solid or liquid and be presented in the pharmaceutical forms commonly used in human medicine, such as for example, plain or sugar-coated tablets, gelatin capsules, granules, suppositories, injectable preparations, ointments, creams, gels; they are prepared according to the usual methods. The active ingredient or ingredients can be incorporated with excipients usually used in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, preservatives. These compositions can also be presented in the form of a lyophilisate intended to be dissolved extemporaneously in an appropriate vehicle for example apyrogenic sterile water.

The dose administered varies according to the condition treated, the patient in question, the administration route and the product considered. It can, for example, be comprised between 0.250 g and 10 g per day, by oral route in adults, with the product described in Example 1, 4 or 5 or also comprised between 0.25 g and 5 g per day by intramuscular or intravenous route. The products of formula (I) can also be used such as disinfectants for surgical instruments.

DETAILED DESCRIPTION

The following examples illustrate the invention.

EXAMPLE 1

Sodium and trifluoroacetate salt of trans 8-(aminomethyl)-2-(2-amino-ethylcarbamoyl)-4,8-dihydro-5-(sulphooxy)-4,7-methano-7H-pyrazolo[3,4-e][1,3]diazepin-6(5H)-one Stage A trans 4,8-dihydro-8-(hydroxymethyl)-5-(phenyl-methoxy)-4,7-methano-7H-pyrazolo[3,4-e][1,3]diazepin-6(5H)-one The methyl trans-4,5,6,8-tetrahydro-6-oxo-5-(phenylmethoxy)-4,7-methano-7H-pyrazolo[3,4-e][1,3]diazepine-8-carboxylate ester described in the application WO2004/052891 (5 g, 15.2 mmol) is put into solution in an anhydrous methanol/tetrahydrofuran mixture 1/1 (100 mL), under nitrogen. $NaBH_4$ (2.3 g, 60.9 mmol) is then added by portions. After stirring overnight at ambient temperature, the reaction mixture is treated with a 10% aqueous solution of $NaH_2PO_4$ (100 mL). After evaporation to dryness, the reaction mixture is taken up in water. The precipitate formed is stirred overnight in ice, then filtered and dried for at least 24 hours under vacuum in the presence of $P_2O_5$, in order to produce the expected compound (3.30 g, 11.0 mmol, 72%) in the form of white powder.

MS (ES+) m/z $[M+H]^+$=301

$^1$H NMR (400 MHz, DMSO-$d_6$): δ(ppm)=3.18-3.50 (ABX, 2H, N—CH$_2$—CH—N), 3.65-3.76 (ABX, 2H, N—CH$_2$—$\overline{OH}$), 4.34 (t, 1H, N—CH—CH$_2$—OH), 4.46 (d, 1$\overline{H, N}$—CH$_2$—CH—N), 4.88 (s, 2$\overline{H,}$ CH$_2$-Ph), 7.29-7.43 (m, 5H, Ph), 7.66 ($\overline{s, 1}$H, H pyrazole), 12.72 (broad, 1H, OH).

Stage B 1,1-dimethylethyl trans [[4,5,6,8-tetrahydro-6-oxo-5-(phenylmethoxy)-4,7-methano-7H-pyrazolo[3,4-e][1,3]diazepin-8-yl]methyl]-carbamate The alcohol obtained in the previous stage (1.73 g, 5.76 mmol) is put into solution in anhydrous pyridine (35 mL) under nitrogen, at 0° C. Then methanesulphonyl chloride (1.78 mL, 23 mmol) is added dropwise. After stirring for 2 hours 30 minutes at ambient temperature, the reaction mixture is treated with a saturated aqueous solution of ammonium chloride (100 mL), then extracted with ethyl acetate. The combined organic phases are then washed 5 times with a saturated aqueous solution of ammonium chloride, dried over sodium sulphate, filtered then concentrated under vacuum in order to produce the expected dimesylated derivative in the form of yellow oil.

The dimesylated intermediate is put into solution in anhydrous dimethylformamide (45 mL), under nitrogen, in the presence of sodium azide (1.12 g, 17.3 mmol). The reaction mixture is heated at 70° C. for 24 hours. If necessary 1 eq. of azide is added so that the conversion is complete. When the reaction is complete, the mixture is treated with a 10% aqueous solution of $NaH_2PO_4$ (100 mL) then extracted with dichloromethane. The combined organic phases are dried over sodium sulphate, filtered then concentrated under vacuum in order to produce the expected azide in the form of yellow oil.

The intermediate is reacted, under nitrogen, in absolute ethanol (17.5 mL). Then di-tert-butyl dicarbonate (1.38 g, 6.34 mmol), triethylsilane (1.38 mL, 8.64 mmol) and 10% palladium hydroxide on carbon (Degussa) (52 mg) are added successively. After being left overnight at ambient temperature, the reaction mixture is filtered then concentrated in order to produce a crude yellow oil. This crude oil is purified by chromatography on a silica column (eluent gradient $CH_2Cl_2$/MeOH 100/0 to 95/5 by 1%) in order to produce the expected compound (1.36 g, 3.40 mmol, 34%) in the form of white solid.

MS (ES+) m/z $[M+H]^+$=401

$^1$H NMR (400 MHz, MeOH-$d_4$): δ(ppm)=1.51 (s, 9H, C(CH$_3$)$_3$), 3.21-3.59 (m, 4H, N—CH$_2$—CH—N and N—CH—$\overline{CH_2}$—NHBoc), 4.36 (m, 1H, N—$\overline{CH}$—CH$_2$—OH), 4.46 (m, $\overline{1H}$, N—CH$_2$—CH—N), 4.99 (A$\overline{B, 2}$H, $\underline{CH_2}$-Ph), 7.41-7.52 (m, 5H, Ph), 7.63 (s, 1H, H pyrazole).

Stage C 1,1-dimethylethyl trans [[2-(2-tert-butoxycarbonylamino-ethylcarbamoyl)-4,5,6,8-tetrahydro-6-oxo-5-(phenylmethoxy)-4,7-methano-7H-pyrazolo[3,4-e][1,3]diazepin-8-yl]methyl]-carbamate Under nitrogen, the derivative obtained in the previous stage (170 mg, 0.426 mmol) is put into solution in dichloromethane (22 mL). At 0° C., triethylamine (119 µl, 0.851 mmol) is added, followed by diphosgene (77 µl, 0.638 mmol) added rapidly dropwise. After 2 hours 30 minutes of stirring at 0° C., N-boc-ethylenediamine (236 µL, 1.49 mmol) is added rapidly and the medium is stirred vigorously at ambient temperature for 1 hour.

The medium is poured into a separating funnel, rinsed with dichloromethane (5 mL), then washed with a 10% aqueous solution of sodium phosphate (15 mL). The aqueous phase is extracted with dichloromethane (15 mL). The organic phases are collected, washed with a saturated solution of NaCl, dried over mgSO$_4$, concentrated under vacuum in order to produce, after chromatography on a silica column (eluent gradient CH$_2$Cl$_2$/ethyl acetate 90/10 to 80/20), the expected derivative (86 mg, 0.147 mmol, 35%).

MS (ES+) m/z [M+H]$^+$=586

$^1$H NMR (400 MHz, CDCl$_3$): δ (ppm)=1.43 (s, 9H, C(CH$_3$)$_3$), 1.47 (s, 9H, C(CH$_3$)$_3$), 3.09 (dd, 1H, N—CH$_2$—CH—N), 3.29-3.40, 3.49-3.59 (m, 6H, CH—CH$_2$—NHBoc, N—CH$_2$—CH$_2$—N, N—CH$_2$—CH$_2$—N), 3.79 (dd, 1H, N—CH$_2$—CH—N), 3.98 (d, 1H, N—CH$_2$—CH—N), 4.59 (m, 1H, CH—CH$_2$—NHBoc), 4.92 (AB, 2H, CH$_2$-Ph), 5.10 (broad, 1H, NH), 6.95 (broad, 1H, NH), 7.40-7.43 (m, 5H, Ph), 8.04 (s, 1H, H pyrazole).

Stage D

Pyridinium salt of the 1,1-dimethylethyl trans [[2-(2-tert-butoxycarbonylamino-ethylcarbamoyl)-4,5,6,8-tetrahydro-6-oxo-5-(sulphooxy)-4,7-methano-7H-pyrazolo[3,4-e][1,3]diazepin-8-yl]methyl]-carbamate Under nitrogen, the derivative obtained in the previous stage (134 mg, 0.229 mmol) is put into solution in dimethylformamide (0.33 mL) and dichloromethane (0.98 mL). 10% palladium on carbon, 50% water-wet (73 mg, 0.034 mmol) is added. After three vacuum/nitrogen purges, the reaction mixture is placed under a hydrogen atmosphere until the disappearance of the starting product according to HPLC. The mixture is then concentrated under vacuum then co-evaporated three times with anhydrous dichloromethane, finally dried under a vacuum bell-jar in the presence of P$_2$O$_5$ for 2 hours, in order to produce the expected debenzylated intermediate.

The debenzylated derivative is taken up in anhydrous pyridine (0.9 mL) in the presence of pyridine/sulphur trioxide complex (73 mg, 0.458 mmol). The reaction mixture is stirred at ambient temperature until complete conversion according to HPLC, then concentrated to dryness after treatment by the addition of water. The crude reaction product is subjected to chromatography on a silica column (eluent gradient CH$_2$Cl$_2$/MeOH 100/0 to 85/15 by 5%) in order to produce the expected salt (79 mg, 0.121 mmol, 53%).

MS (ES(−)): m/z [M−H]$^−$=574

$^1$H NMR (400 MHz, MeOH-d$_4$): δ (ppm)=1.25 (s, 9H, C(CH$_3$)$_3$), 1.32 (s, 9H, C(CH$_3$)$_3$), 3.05-3.16, 3.22-3.32, 3.39-3.54 (m, 8H, N—CH$_2$—CH—N, CH—CH$_2$—NHBoc, N—CH$_2$—CH$_2$—N, N—CH$_2$—CH$_2$—N), 4.40 (m, 1H, CH—CH$_2$—NHBoc), 4.78 (d, 1H, N—CH$_2$—CH—N), 7.39 (broad, 1H, NH), 7.84 (m, 2H, Py), 8.07 (s, 1H, H pyrazole), 8.20 (broad, 1H, NH), 8.48 (m, 1H, Py), 8.66 (m, 2H, Py), 9.02 (broad, 1H, NH)

Stage E

Sodium salt of 1,1-dimethylethyl trans [[2-(2-tert-butoxycarbonylamino-ethylcarbamoyl)-4,5,6,8-tetrahydro-6-oxo-5-(sulphooxy)-4,7-methano-7H-pyrazolo[3,4-e][1,3]diazepin-8-yl]methyl]-carbamate A suspension of 10 g of DOWEX 50WX8 resin in a 2N solution of soda (50 mL) is stirred for 1 hour, then poured onto a chromatography column. The column is conditioned with demineralized water until a neutral pH is reached, then with a water/THF mixture 90/10. The salt obtained in the previous stage (79 mg, 0.121 mmol) is dissolved in a minimum amount of methanol, deposited on the column, then eluted with a water/THF mixture 90/10. The fractions containing the substrate are combined and frozen. The frozen solution is lyophilized in order to produce the expected sodium salt (65 mg, 0.109 mmol, 90%) in the form of a beige solid.

MS (ES(−)): m/z [M−H]$^−$=574

$^1$H NMR (400 MHz, DMSO-d$_6$): δ (ppm)=1.36 (s, 9H, C(CH$_3$)$_3$), 1.41 (s, 9H, C(CH$_3$)$_3$), 3.05-3.13, 3.16-3.46 (m, 8H, N—CH$_2$—CH—N, CH—CH$_2$—NHBoc, N—CH$_2$—CH$_2$—N, N—CH$_2$—CH$_2$—N), 4.38 (m, 1H, CH—CH$_2$—NHBoc), 4.76 (d, 1H, N—CH$_2$—CH—N), 6.93 (broad, 1H, NH), 7.13 (broad, 1H, NH), 8.17 (s, 1H, H pyrazole), 8.42 (broad, 1H, NH)

Stage F

Sodium and trifluoroacetate salt of trans 8-(aminomethyl)-2-(2-amino-ethylcarbamoyl)-4,8-dihydro-5-(sulphooxy)-4,7-methano-7H-pyrazolo[3,4-e][1,3]diazepin-6(5H)-one A solution of trifluoroacetic acid (2.4 mL) in dichloromethane (2.4 mL) is added dropwise to a solution of the sodium salt obtained in the previous stage (42 mg, 0.092 mmol) in dichloromethane (1.2 mL) under nitrogen and cooled down to 0° C. Stirring is maintained at ambient temperature for 1 hour at ambient temperature. The mixture is evaporated to dryness. The residue is taken up in water (3 mL) and the solution is washed with diethyl ether (3 mL). The aqueous solution is frozen then lyophilized in order to produce the expected sodium and trifluoroacetate salt (62 mg, 0.099 mmol, 94%) in the form of a beige solid.

MS (ES(−)): m/z [M−H]$^−$=374

$^1$H NMR (400 MHz, DMSO-d$_6$): δ (ppm)=2.98-3.70 (m, 8H, N—CH$_2$—CH—N, CH—CH$_2$—NH$_3$$^+$, N—CH$_2$—CH$_2$—N,N—CH$_2$—CH$_2$—N), 4.72 (m, 1H, CH—CH$_2$—NH$_3$$^+$), 4.88 (d, 1H, N—CH$_2$—CH—N), 7.76 (broad, 3H, NH$_3$$^+$), 8.16 (broad, 3H, NH$_3$$^+$), 8.32 (s, 1H, H pyrazole), 8.59 (broad, 1H, NH)

EXAMPLE 2

Sodium and trifluoroacetate salt of trans 8-(aminomethyl)-2-(4-piperazine-1-carbonyl)-4,8-dihydro-5-(sulphooxy)-4,7-methano-7H-pyrazolo[3,4-e][1,3]diazepin-6(5H)-one Stage A 1,1-dimethylethyl trans [[2-(4-tert-butoxycarbonyl-piperazine-1-carbonyl)-4,5,6,8-tetrahydro-6-oxo-5-(phenylmethoxy)-4,7-methano-7H-pyrazolo[3,4-e][1,3]diazepin-8-yl]methyl]-carbamate By proceeding as indicated in Stage C of Example 1, the derivative obtained in the previous stage (150 mg, 0.376 mmol), dichloromethane (20 mL), triethylamine (105 μL, 0.751 mmol), diphosgene (68 μL, 0.563 mmol) and N-boc-piperazine (210 mg, 1.13 mmol), after chromatography on a silica column (eluent gradient CH$_2$Cl$_2$/ethyl acetate 80/20 to 70/30), produce the expected derivative (145 mg, 0.237 mmol, 63%) in the form of a beige solid.

MS (ES+) m/z [M+H]$^+$=612

$^1$H NMR (400 MHz, CDCl$_3$): δ (ppm)=1.45 (s, 9H, C(CH$_3$)$_3$), 1.48 (s, 9H, C(CH$_3$)$_3$), 3.07 (dd, 1H, N—CH$_2$—CH—N), 3.33 (m, 2H, CH—CH$_2$—NHBoc), 3.51 (m, 4H, N—CH$_2$—CH$_2$—N), 3.77 (m, 5H, N—CH$_2$—CH$_2$—N,N—CH$_2$—CH—N), 4.00 (d, 1H, N—CH$_2$—

CH—N), 4.60 (m, 1H, CH—CH₂—NHBoc), 4.92 (AB, 1H, CH₂-Ph), 5.13 (broad, 1H, NH), 7.38-7.43 (m, 5H, Ph), 7.98 (s, 1H, H pyrazole).

Stage B

Pyridinium salt of 1,1-dimethylethyl trans [[2-(4-tert-butoxycarbonyl-piperazine-1-carbonyl)-4,5,6,8-tetrahydro-6-oxo-5-(sulphooxy)-4,7-methano-7H-pyrazolo[3,4-e][1,3]diazepin-8-yl]methyl]-carbamate By proceeding as indicated in Stage D of Example 1, the derivative obtained in the previous stage (145 mg, 0.237 mmol), dimethylformamide (0.34 mL), dichloromethane (1.0 mL) and 10% palladium on carbon, 50% water-wet (76 mg, 0.036 mmol) produce the expected debenzylated intermediate.

The debenzylated intermediate, pyridine (1.0 mL) and pyridine/sulphur trioxide complex (112 mg, 0.702 mmol), after chromatography on a silica column (eluent gradient CH₂Cl₂/MeOH 100/0 to 80/20 by 5%) produce the expected derivative (40 mg, 0.059 mmol, 21%) in the form of a beige solid.

MS (ES(−)): m/z [M−H]⁻=600

¹H NMR (400 MHz, CDCl₃): δ (ppm)=1.42 (s, 9H, C(CH₃)₃), 1.47 (s, 9H, C(CH₃)₃), 3.02-3.28, 3.40-3.90 (m, 12H, N—CH₂—CH—N, CH—CH₂—NHBoc, N—CH₂—CH₂—N,N—CH₂—CH₂—N), 4.58 (m, 1H, CH—CH₂—NHBoc), 4.97 (d, 1H, N—CH₂—CH—N), 7.28 (s, 1H, H pyrazole), 8.12 (broad, 1H, NH)

Stage C

Sodium salt of 1,1-dimethylethyl trans [[2-(4-tert-butoxycarbonyl-piperazine-1-carbonyl)-4,5,6,8-tetrahydro-6-oxo-5-(sulphooxy)-4,7-methano-7H-pyrazolo[3,4-e][1,3]diazepin-8-yl]methyl]-carbamate By proceeding as indicated in Stage E of Example 1, the salt obtained in the previous stage (40 mg, 0.059 mmol), DOWEX 50WX8 resin (5 g) and 2N soda (25 mL) produce the expected sodium salt (32 mg, 0.051 mmol, 87%) in the form of a beige solid.

MS (ES(−)): m/z [M−H]⁻=600

¹H NMR (400 MHz, DMSO-d₆): δ (ppm)=1.40 (s, 9H, C(CH₃)₃), 1.41 (s, 9H, C(CH₃)₃), 3.26-3.65 (m, 12H, N—CH₂—CH—N, CH—CH₂—NHBoc, N—CH₂—CH₂—N,N—CH₂—CH₂—N), 4.42 (m, 1H, CH—CH₂—NHBoc), 4.78 (d, 1H, N—CH₂—CH—N), 7.06 (broad, 1H, NH), 8.13 (s, 1H, H pyrazole)

Stage D

Sodium and trifluoroacetate salt of trans 8-(aminomethyl)-2-(piperazine-1-carbonyl)-4,8-dihydro-5-(sulphooxy)-4,7-methano-7H-pyrazolo[3,4-e][1,3]diazepin-6(5H)-one By proceeding as indicated in Stage F of Example 1, the sodium salt obtained in the previous stage (126 mg, 0.203 mmol), dichloromethane (3.6 mL), trifluoroacetic acid (7.2 mL) in dichloromethane (7.2 mL) produce the expected sodium and trifluoroacetate salt (124 mg, 0.191 mmol, 95%) in the form of a beige solid.

¹H NMR (400 MHz, DMSO-d₆): δ (ppm)=3.18-3.27, 3.37-3.43, 3.84-3.93 (m, 12H, N—CH₂—CH—NH₃⁺, CH—CH₂—N,N—CH₂—CH₂—N, N—CH₂—CH₂—N), 4.69 (m, 1H, CH—CH₂—NH₃⁺), 4.88 (d, 1H, N—CH₂—CH—N), 8.13 (broad, 3H, NH₃⁺), 8.24 (s, 1H, H pyrazole), 9.00 (broad, 2H, NH₂⁺)

EXAMPLE 3

Sodium and trifluoroacetate salt of trans 8-(aminomethyl)-4,8-dihydro-2-(2-dimethylaminoethyl carbamoyl)-5-(sulphooxy)-4,7-methano-7H-pyrazolo[3,4-e][1,3] diazepin-6(5H)-one Stage A 1,1-dimethylethyl trans [[2-(2-dimethylamino-ethyl-carbamoyl)-4,5,6,8-tetrahydro-6-oxo-5-(phenyl-methoxy)-4,7-methano-7H-pyrazolo[3,4-e][1,3]diazepin-8-yl]methyl]-carbamate By proceeding as indicated in Stage C of Example 1, the derivative obtained in Stage B of Example 1 (228 mg, 0.571 mmol), dichloromethane (30 mL), triethylamine (159 µL, 1.14 mmol), diphosgene (103 µL, 0.856 mmol) and N,N-dimethyl-ethylenediamine (317 µL, 2.85 mmol), after chromatography on a silica column (eluent gradient CH₂Cl₂/MeOH 100/0 to 95/5 by 1%), produce the expected derivative (193 mg, 0.375 mmol, 66%) in the form of a yellow solid.

MS (ES+) m/z [M+H]⁺=514

¹H NMR (400 MHz, CDCl₃): δ (ppm)=1.46 (s, 9H, C(CH₃)₃), 2.30 (s, 3H, CH₃), 2.31 (s, 3H, CH₃), 2.53 (m, 2H, N—CH₂—CH₂—NMe₂), 3.08 (dd, 1H, N—CH₂—CH—N), 3.38 (m, 2H, CH—CH₂—NHBoc), 3.48 (m, 2H, N—CH₂—CH₂—NMe₂), 3.80 (dd, 1H, N—CH₂—CH—N), 3.98 (d, 1H, N—CH₂—CH—N), 4.60 (m, 1H, CH—CH₂—NHBoc), 4.92 (AB, 2H, CH₂-Ph), 5.16 (broad, 1H, NH), 7.39-7.43 (m, 5H, Ph), 8.04 (s, 1H, H pyrazole).

Stage B

Pyridinium salt of 1,1-dimethylethyl trans [[2-(2-dimethylamino-ethylcarbamoyl)-4,5,6,8-tetrahydro-6-oxo-5-(sulphooxy)-4,7-methano-7H-pyrazolo[3,4-e][1,3]diazepin-8-yl]methyl]-carbamate By proceeding as indicated in Stage D of Example 1, the derivative obtained in the previous stage (173 mg, 0.337 mmol), dimethylformamide (0.48 mL), dichloromethane (1.44 mL) and 10% palladium on carbon, 50% water-wet (108 mg, 0.051 mmol) produce the expected debenzylated intermediate.

The debenzylated intermediate, pyridine (1.1 mL) and pyridine/sulphur trioxide complex (107 mg, 0.673 mmol), after chromatography on a silica column (eluent gradient CH₂Cl₂/MeOH 100/0 to 85/15 by 5%) produce the expected derivative (107 mg, 0.184 mmol, 55%) in the form of a beige solid.

MS (ES(−)): m/z [M−H]⁻=574

¹H NMR (400 MHz, MeOH-d₄): δ (ppm)=1.52 (s, 9H, C(CH₃)₃), 3.04 (s, 6H, 2×CH₃), 3.48 (m, 4H, CH—CH₂—NHBoc, N—CH₂—CH₂—NMe₂), 3.61 (d, 1H, N—CH₂—CH—N), 3.72 (dd, 1H, N—CH₂—CH—N), 4.82 (m, 2H, N—CH₂—CH₂—NMe₂), 4.65 (m, 1H, CH—CH₂—NHBoc), 4.95 (d, 1H, N—CH₂—CH—N), 8.28 (s, 1H, H pyrazole)

Stage C

Sodium salt of 1,1-dimethylethyl trans [[2-(2-dimethylamino-ethylcarbamoyl)-4,5,6,8-tetrahydro-6-oxo-5-(sulphooxy)-4,7-methano-7H-pyrazolo[3,4-e][1,3]diazepin-8-yl]methyl]-carbamate By proceeding as indicated in Stage E of Example 1, the salt obtained in the previous stage (107 mg, 0.184 mmol), DOWEX 50WX8 resin (13 g) and 2N soda (65 mL) produce the expected sodium salt (87 mg, 0.166 mmol, 91%) in the form of a beige solid.

MS (ES+) m/z [M+H]$^+$=504

$^1$H NMR (400 MHz, DMSO-d$_6$): δ (ppm)=1.41 (s, 9H, C(CH$_3$)$_3$), 3.24-3.43 (m, 14H, 2×CH$_3$, CH—CH$_2$—NHBoc, N—CH$_2$—CH$_2$—NMe$_2$, N—CH$_2$—CH—N,N—CH$_2$—CH$_2$—NMe$_2$), 4.40 (m, 1H, CH—CH$_2$—NHBoc), 4.78 (d, 1H, N—CH$_2$—CH—N), 7.15 (broad, 1H, NH), 8.20 (s, 1H, H pyrazole)

Stage D

Sodium and trifluoroacetate salt of trans 8-(aminomethyl)-4,8-dihydro-2-(2-dimethylamino-ethylcarbamoyl)-5-(sulphooxy)-4,7-methano-7H-pyrazolo[3,4-e][1,3] diazepin-6(5H)-one By proceeding as indicated in Stage F of Example 1, the sodium salt obtained in the previous stage (87 mg, 0.166 mmol), dichloromethane (2.5 mL), trifluoroacetic acid (5.0 mL) in dichloromethane (5.0 mL) produce the expected sodium and trifluoroacetate salt (76 mg, 0.141 mmol, 85%) in the form of a beige solid.

MS (ES(−)): m/z [M−H]$^−$=402

$^1$H NMR (400 MHz, DMSO-d$_6$): δ (ppm)=2.17 (s, 6H, 2×CH3), 3.12-3.72 (m, 8H, N—CH$_2$—CH—N, CH—CH$_2$—NH$_3^+$, N—CH$_2$—CH$_2$—NMe$_2$, N—CH$_2$—CH$_2$—NMe$_2$), 4.73 (dd, 1H, CH—CH$_2$—NH$_3^+$), 4.88 (d, 1H, N—CH$_2$—CH—N), 8.17 (broad, 3H, NH$_3^+$), 8.32 (s, 1H, H pyrazole), 8.63 (broad, 1H, NH)

EXAMPLE 4

Sodium and trifluoroacetate salt of trans 8-(aminomethyl)-4,8-dihydro-2-(pyrrolidine-1-carbonyl)-5-(sulphooxy)-4,7-methano-7H-pyrazolo[3,4-e][1,3] diazepin-6(5H)-one Stage A 1,1-dimethylethyl trans [[4,5,6,8-tetrahydro-6-oxo-5-(phenylmethoxy)-2-(pyrrolidine-1-carbonyl)-4,7-methano-7H-pyrazolo[3,4-e][1,3]diazepin-8-yl]methyl]-carbamate By proceeding as indicated in Stage C of Example 1, the derivative obtained in Stage B of Example 1 (150 mg, 0.376 mmol), dichloromethane (20 mL), triethylamine (105 μL, 0.751 mmol), diphosgene (68 μL, 0.563 mmol) and pyrrolidine (157 μL, 1.88 mmol), after chromatography on a silica column (eluent CH$_2$Cl$_2$/ethyl acetate 85/15), produce the expected derivative (143 mg, 0.288 mmol, 76%) in the form of a beige solid.

MS (ES+) m/z [M+H]$^+$=497

$^1$H NMR (400 MHz, CDCl$_3$): δ (ppm)=1.47 (s, 9H, C(CH$_3$)$_3$), 1.89 (m, 4H, N—CH$_2$—CH$_2$pyrrolidine), 3.08 (dd, 1H, N—CH$_2$—CH—N), 3.36 (dd, 1H, N—CH$_2$—CH—N), 3.45 (m, 1H, CH—CH$_2$—NHBoc), 3.65 (m, 2H, N—CH$_2$—CH$_2$—Npyrrolidine), 3.79 (m, 1H, CH—CH$_2$—NHBoc), 3.92 (m, 2H, N—CH$_2$—CH$_2$—Npyrrolidine), 3.99 (d, 1H, N—CH$_2$—CH—N), 4.63 (m, 1H, CH—CH$_2$—NHBoc), 4.94 (AB, 2H, CH$_2$-Ph), 5.16 (broad, 1H, NH), 7.39-7.43 (m, 5H, Ph), 8.11 (s, 1H, H pyrazole).

Stage B

Pyridinium salt of 1,1-dimethylethyl trans [[4,5,6,8-tetrahydro-6-oxo-2-(pyrrolidine-1-carbonyl)-5-(sulphooxy)-4,7-methano-7H-pyrazolo[3,4-e][1,3]diazepin-8-yl]methyl]-carbamate By proceeding as indicated in Stage D of Example 1, the derivative obtained in the previous stage (143 mg, 0.288 mmol), dimethylformamide (0.41 mL), dichloromethane (1.23 mL) and 10% palladium on carbon, 50% water-wet (92 mg, 0.043 mmol) produce the expected debenzylated intermediate.

The debenzylated intermediate, pyridine (0.93 mL) and pyridine/sulphur trioxide complex (88 mg, 0.553 mmol), after chromatography on a silica column (eluent gradient CH$_2$Cl$_2$/MeOH 100/0 to 85/15 by 5%) produce the expected derivative (76 mg, 0.134 mmol, 49%) in the form of a beige solid.

MS (ES(−)): m/z [M−H]$^−$=485

$^1$H NMR (400 MHz, MeOH-d$_4$): δ (ppm)=1.51 (s, 9H, C(CH$_3$)$_3$), 2.00 (m, 4H, N—CH$_2$—CH$_2$pyrrolidine), 3.49 (dd, 1H, N—CH$_2$—CH—N), 3.57 (dd, 1H, N—CH$_2$—CH—N), 3.65 (m, 4H, N—CH$_2$—CH$_2$—Npyrrolidine), 3.96 (m, 2H, CH—CH$_2$—NHBoc), 4.67 (m, 1H, CH—CH$_2$—NHBoc), 4.98 (d, 1H, N—CH$_2$—CH—N), 8.30 (s, 1H, H pyrazole)

Stage C

Sodium salt of 1,1-dimethylethyl trans [[4,5,6,8-tetrahydro-6-oxo-2-(pyrrolidine-1-carbonyl)-5-(sulphooxy)-4,7-methano-7H-pyrazolo[3,4-e][1,3]diazepin-8-yl]methyl]-carbamate By proceeding as indicated in Stage E of Example 1, the derivative obtained in the previous stage (76 mg, 0.134 mmol), DOWEX 50WX8 resin (9 g) and 2N soda (45 mL) produce the expected sodium salt (64 mg, 0.126 mmol, 93%) in the form of a beige solid.

MS (ES(+)): m/z [M+H]$^+$=486

$^1$H NMR (400 MHz, DMSO-d$_6$): δ (ppm)=1.39 (s, 9H, C(CH$_3$)$_3$), 1.84 (m, 4H, N—CH$_2$—CH$_2$pyrrolidine), 3.25-3.40 (m, 4H, N—CH$_2$—CH—N,N—CH$_2$—CH$_2$—Npyrrolidine), 3.54 (m, 2H, N—CH$_2$—CH$_2$—Npyrrolidine), 3.79 (m, 2H, CH—CH$_2$—NHBoc), 4.41 (m, 1H, CH—CH$_2$—NHBoc), 4.78 (d, 1H, N—CH$_2$—CH—N), 7.05 (broad, 1H, NH), 8.16 (s, 1H, H pyrazole)

Stage D

Sodium and trifluoroacetate salt of trans-8-(aminomethyl)-4,8-dihydro-2-(pyrrolidine-1-carbonyl)-5-(sulphooxy)-4,7-methano-7H-pyrazolo[3,4-e][1,3] diazepin-6(5H)-one By proceeding as indicated in Stage F of Example 1, the sodium salt obtained in the previous stage (64 mg, 0.126 mmol), dichloromethane (1.8 mL), trifluoroacetic acid (3.7 mL) in dichloromethane (3.7 mL) produce the expected sodium and trifluoroacetate salt (57 mg, 0.109 mmol, 86%) in the form of a beige solid.

MS (ES(−)): m/z [M−H]⁻=385

¹H NMR (400 MHz, DMSO-d₆): δ (ppm)=1.85 (m, 4H, N—CH₂—CH₂pyrrolidine), 3.42-3.74 (m, 8H, N—CH₂—CH=N, N—CH₂—CH₂—Npyrrolidine, CH—CH₂—NH₃⁺), 4.68 (m, 1H, CH—CH₂—NH₃⁺), 4.86 (d, 1H, N=CH₂—CH—N), 8.09 (broad, 3H, NH₃⁺), 8.26 (s, 1H, H pyrazole)

EXAMPLE 5

Sodium and trifluoroacetate salt of trans 8-(aminomethyl)-2-[(3-amino-propyl)carbamoyl]-4,8-dihydro-5-(sulphooxy)-4,7-methano-7H-pyrazolo[3,4-e][1,3]diazepin-6(5H)-one Stage A 1,1-dimethylethyl trans 2-[(3-tert-butoxycarbonylamino-propyl)carbamoyl]-4,5,6,8-tetrahydro-5-(phenylmethoxy)-4,7-methano-7H-pyrazolo[3,4-e][1,3]diazepin-8-yl]methyl]-carbamate By proceeding as indicated in Stage C of Example 1, the derivative obtained in Stage B of Example 1 (250 mg, 0.626 mmol), dichloromethane (32.8 mL), triethylamine (174 μL), diphosgene (113 μL) and N-Boc-1,3-propanediamine (382 μL), after a reaction time of 3 hours 30 minutes (~40% conversion) and chromatography on a silica column (eluent gradient CH₂Cl₂/AcOEt 100/0 to 70/30), produce the expected derivative (132 mg, 0.22 mmol, 35%).

MS (ES+) m/z [M+H]⁺=600

¹H NMR (400 MHz, CDCl₃): δ(ppm)=1.48 (s, 9H, ᵗBu), 1.61 (s, 9H, ᵗBu), 1.79 (m, 2h, NHCH₂—CH₂—CH₂—NHBOC), 3.05-3.75 (m+2 ABX, 8H, N—CH₂—CH—N, N—CH—CH₂—NHBOC, NH CH₂—CH₂—CH₂—NHBOC, NHCH₂—CH₂—CH₂—NHBOC), 4.00 (d, 1H, N—CH—CH₂—NHBOC), 4.62 (dd, 1H, N—CH₂—CH—N), 4.97 (AB, 2H, CH₂-Ph), 7.42-7.45 (m, 5H, Ph), 8.05 (s, 1H, H pyrazole).

Stage B

Sodium salt of 1,1-dimethylethyl trans 2-[(3-tert-butoxycarbonylamino-propyl)carbamoyl]-4,5,6,8-tetrahydro-5-(sulphooxy)-4,7-methano-7H-pyrazolo[3,4-e][1,3]diazepin-8-yl]methyl]-carbamate By proceeding as indicated in Stage D of Example 1, the derivative obtained in the previous stage (132 mg, 0.22 mmol), the dimethylformamide/dichloromethane mixture 1/3 (2.5 mL) and 10% palladium on carbon, 50% water-wet (53 mg) produce the expected debenzylated intermediate.

The debenzylated intermediate, pyridine (0.86 mL) and pyridine/sulphur trioxide complex (70 mg, 0.44 mmol), after chromatography on a silica column (eluent gradient CH₂Cl₂/MeOH 100/0 to 80/20), produce the expected derivative (90 mg, 0.134 mmol, 61%) in the form of a white solid.

By proceeding as indicated in Stage E of Example 1, the salt obtained in the previous stage (90 mg, 0.134 mmol), DOWEX 50WX8 resin (11 g) and 2N soda (55 mL), after elution with water only and lyophilization, produce the expected sodium salt (48 mg, 0.078 mmol, 58%) in the form of a white powder.

MS (ES+) m/z [M−H]⁻=588

¹H NMR (400 MHz, MeOH-d₄): δ (ppm)=1.49 (s, 9H, C(CH₃)₃), 1.52 (s, 9H, C(CH₃)₃), 1.81 (m, 2H, NCH₂—CH₂—CH₂—NHBoc), 3.18 (m, 2H, NCH₂—CH₂-CH₂—NHBoc), 3.36-3.45 (m, 6H, N CH₂—CH₂—CH₂—NHBoc, N—CH₂—CH—N and CH—CH₂—NHBoc), 4.65 (dd, 1H, CH—CH₂—NHBoc), 4.99 (d, 1H, N—CH₂—CH—N), 8.29 (s, 1H, H pyrazole).

Stage C

Sodium and trifluoroacetate salt of trans 8-(aminomethyl)-2-[(3-amino-propyl)carbamoyl]-4,8-dihydro-5-(sulphooxy)-4,7-methano-7H-pyrazolo[3,4-e][1,3]diazepin-6(5H)-one By proceeding as indicated in Stage F of Example 1, the sodium salt obtained in the previous stage (48 mg, 0.078 mmol), dichloromethane (1.34 mL), the trifluoroacetic acid/dichloromethane mixture (5.36 mL) produce the expected sodium and trifluoroacetate salt (45 mg, 0.070 mmol, 90%) in the form of a beige powder.

MS (ES+) m/z [M−H]⁻=390

¹H NMR (400 MHz, MeOH-d₄): δ (ppm)=1.86 (m, 2H, NCH₂—CH₂—CH₂—NH₂), 2.91 (m, 2H, NCH₂—CH₂—CH₂—NH₂), 3.29-3.80 (m, 6H, N CH₂—CH₂—CH₂—NH₂, N—CH₂—CH—N and CH—CH₂—NH₂), 4.65 (dd, 1H, CH—CH₂—NH₂), 4.86 (d, 1H, N—CH₂—CH—N), 8.18 (s, 1H, H pyrazole).

EXAMPLE 6

Sodium and trifluoroacetate salt of trans 8-(aminomethyl)-2-[(3-amino-butyl)carbamoyl]-4,8-dihydro-5-(sulphooxy)-4,7-methano-7H-pyrazolo[3,4-e][1,3]diazepin-6(5H)-one Stage A 1,1-dimethylethyl trans 2-[(3-tert-butoxycarbonylamino-butyl)carbamoyl]-4,5,6,8-tetrahydro-6-oxo-5-(phenylmethoxy)-4,7-methano-7H-pyrazolo[3,4-e][1,3]diazepin-8-yl]methyl]-carbamate By proceeding as indicated in Stage C of Example 1, the derivative obtained in Stage B of Example 1 (250 mg, 0.626 mmol), dichloromethane (32.8 mL), triethylamine (174 μL), diphosgene (113 μL) and N-Boc-1,3-butanediamine (419 μL), after a reaction time of 3 hours 30 minutes (~50% conversion) and chromatography on a silica column (eluent gradient CH₂Cl₂/AcOEt 100/0 to 70/30), produce the expected derivative (91 mg, 0.148 mmol, 24%).

MS (ES+) m/z [M+H]⁺=614

¹H NMR (400 MHz, CDCl₃): δ(ppm)=1.47 (s, 9H, ᵗBu), 1.48 (s, 9H, ᵗBu), 1.58-1.68 (m, 4H, NHCH₂—CH₂—CH₂—CH₂—NHBoc and NHCH₂—CH₂—CH₂—CH₂—NHBoc), 3.05-3.55 (m+2 ABX, 8H, N—CH₂—CH—N,N—CH—CH₂—NHBoc, NH CH₂—CH₂—CH₂—CH₂—NHBoc, NHCH₂—CH₂—CH₂—CH₂—NHBoc), 4.00 (d, 1H, N—CH—CH₂—NHBoc), 4.60 (dd, 2H, N—CH₂—CH—N), 4.97 (AB, 2H, CH₂-Ph), 5.05 (bs, 1H, NH), 7.05 (bs, 1H, NH), 7.42-7.45 (m, 5H, Ph), 8.05 (s, 1H, H pyrazole).

Stage B

Sodium salt of 1,1-dimethylethyl trans 2-[(3-tert-butoxycarbonylamino-butyl)carbamoyl]-4,5,6,8-tetrahydro-6-oxo-5-(sulphooxy)-4,7-methano-7H-pyrazolo[3,4-e][1,3]diazepin-8-yl]methyl]-carbamate By proceeding as indicated in Stage D of Example 1, the derivative obtained in the previous stage (91 mg, 0.15 mmol), the dimethylformamide/dichloromethane mixture 1/3 (1.7 mL) and 10% palladium on carbon, 50% water-wet (36 mg) produce the expected debenzylated intermediate.

The debenzylated intermediate, pyridine (0.86 mL) and pyridine/sulphur trioxide complex (47 mg), after chromatography on a silica column (eluent gradient $CH_2Cl_2/MeOH$ 95/5 to 90/10), produce the expected derivative (38 mg, 0.056 mmol, 37%).

By proceeding as indicated in Stage E of Example 1, the salt obtained in the previous stage (38 mg, 0.056 mmol), DOWEX 50WX8 resin (4.6 g) and 2N soda (23 mL), after elution with water only and lyophilization produce the expected sodium salt (43 mg, 0.068 mmol, 100%) in the form of a white powder.

MS (ES+) m/z $[M-H]^-=602$ $^1H$ NMR (400 MHz, MeOD-$d_4$): δ(ppm)=1.50 (s, 9H, $^tBu$), 1.53 (s, 9H, $^tBu$), 1.59 (m, 2H, $NHCH_2$—$CH_2$—$CH_2$—$CH_2$—NHBoc), 1.68 (m, 2H, $NHCH_2$—$\overline{CH_2}$—$CH_2$—$CH_2$—NHBoc), 3.11-3.82 (m+2 ABX, 8H, $\overline{N}$=$CH_2$—CH—N,N—CH—$CH_2$—NHBoc, NH $CH_2$=$\overline{CH_2}$—$CH_2$—$CH_2$—$N\overline{H}Boc$, $NHCH_2$—$CH_2$—$\overline{CH_2}$—$CH_2$—NHBoc), 4.45 (bs, 1H, NH), 4.62 (dd, 1H, N—CH—$CH_2$—NHBoc), 5.00 (dd, 2H, N—$CH_2$—CH—N), 5.45 (bs, 1H, NH), 8.05 (s, 1H, H pyrazole), 8.38 (bs, 1H, NH).

Stage C

Sodium and trifluoroacetate salt of trans 8-(aminoethyl)-2[(3-amino-butyl)carbamoyl]-4,8-dihydro-5-(sulphooxy)-4,7-methano-7H-pyrazolo[3,4-e][1,3]diazepin-6(5H)-one By proceeding as indicated in Stage F of Example 1, the sodium salt obtained in the previous stage (43 mg, 0.068 mmol), dichloromethane (1.17 mL), the trifluoroacetic acid/dichloromethane mixture (4.68 mL) produce the expected sodium and trifluoroacetate salt (40 mg, 0.064 mmol, 93%) in the form of a beige powder.

MS (ES+) m/z $[M+H]^-=404$ $^1H$ NMR (400 MHz, MeOD-$d_4$): δ(ppm)=1.20 (m, 2H, $NHCH_2$—$CH_2$—$CH_2$—$CH_2$—$NH_2$), 1.60 (m, 2H, $NHCH_2$—$CH_2$—$\overline{CH_2}$—$CH_2$—$NH_2$), 2.70-3.72 (m+2 ABX, 8H, $N$=$CH_2$—CH—N,N—CH—$CH_2$—$NH_2$, NH $CH_2$—$CH_2$—$\overline{CH_2}$—$CH_2$—$NH_2$, $NH\overline{CH_2}$—$CH_2$—$CH_2$—$\overline{CH_2}$—$NH_2$), 4.80 (dd, 2H, N—$CH_2$—CH—N), 8.20 (s, 1H, $\overline{H}$ pyrazole).

EXAMPLE 7

Sodium and trifluoroacetate salt of trans 8-(aminoethyl)-2-(carbamoylmethyl-carbamoyl)-4,8-dihydro-5-(sulphooxy)-4,7-methano-7H-pyrazolo[3,4-e][1,3]diazepin-6(5H)-one

Stage A

1,1-dimethylethyl trans [[2-(carbamoylmethyl-carbamoyl)-4,5,6,8-tetrahydro-6-oxo-5-(phenylmethoxy)-4,7-methano-7H-pyrazolo[3,4-e][1,3]diazepin-8-yl]methyl]-carbamate By proceeding as indicated in Stage C of Example 1, the derivative obtained in Stage B of Example 1 (200 mg, 0.501 mmol), dichloromethane (26 mL), triethylamine (0.489 mL, 3.507 mmol), diphosgene (0.091 mL, 0.751 mmol) and glycinamide hydrochloride salt (0.277 mg, 2.50 mmol), after reaction for 2 hours and chromatography on a silica column of this crude product combined with another obtained from 50 mg of starting substrate (0.125 mmol) (eluent gradient $CH_2Cl_2/AcOEt$ 100/0 to 00/100), produce the expected derivative (115 mg, 0.23 mmol, 36.8%).

MS (ES(+): m/z $[M+H]^+=500$ $^1H$ NMR (400 MHz, $CDCl_3$): δ (ppm)=1.48 (s, 9H, $C(CH_3)_3$), 3.10-3.20 (AB, 1H, N—$CH_2$—CH—N), 3.36-3.39 (m, 2H, N—$CH_2$—CH—N and CH—$CH_2$—NH-Boc), 3.8 (broad, 1H, CH—$CH_2$—NHBoc), 4.03 (d, 1H, N—$CH_2$—CH—N), 4.90 (m, 2H, N—$CH_2$—CO—N), 4.60-4.70 (broad, 1H, N—CH—$CH_2$—NHBoc), 4.88-5.05 (AB, 2H, N—O—$CH_2$-Ph), 5.20 (broad, 1H, NH), 5.65 (broad, 1H, CO—$NH_2$), 6.15 (broad, 1H, CO—$NH_2$), 7.42-7.45 (m, 5H, Ph), 7.65 (broad, 1H, NH), 8.07 (s, 1H, H pyrazole).

Stage B

Pyridinium salt of 1,1-dimethylethyl trans [[2-(carbamoylmethyl-carbamoyl)-4,5,6,8-tetrahydro-6-oxo-5-(sulphooxy)-4,7-methano-7H-pyrazolo[3,4-e][1,3]diazepin-8-yl]methyl]-carbamate By proceeding as indicated in Stage D of Example 1, the derivative obtained in the previous stage (110 mg, 0.22 mmol), dimethylformamide (0.32 mL), dichloromethane (0.96 mL) and 10% palladium on carbon, 50% water-wet (70.3 mg, 0.033 mmol) produce the expected debenzylated intermediate. (MS (ES(+): m/z $[M+H]^+=409$)

The debenzylated intermediate, pyridine (0.69 mL) and pyridine/sulphur trioxide complex (70 mg, 0.440 mmol), after chromatography on a silica column (4 g, eluent $CH_2Cl_2/MeOH$ 100/0 to 80/20), produce the expected product but still with insufficient purity. The latter is returned to solution in water. The aqueous solution is extracted with dichloromethane (2 mL, 3 times), then the aqueous phase is frozen and lyophilized in order to produce the expected compound (65 mg, 0.114 mmol, 52%) in the form of a white solid.

MS ((ES(−)): m/z $[M−H]^-=488$ $^1H$ NMR (400 MHz, DMSO-$d_{6+}$, 1 drop $D_2O$): δ (ppm)= 1.38 (s, 9H, $C(CH_3)_3$), 3.30-3.44 (m, 4H, N—$CH_2$—CH—N and CH—$CH_2$—NHBoc), 3.67-4.00 (m, 2H, N—$CH_2$—CO—N), 4.40 (m, 1H, N—$CH_2$—CH—N), 4.79 (broad, 1H, N—CH—$CH_2$—NHBoc), 7.83-7.84 (m, 2H, Pyridine), 8.20 (s, 1H, H pyrazole); 8.32-8.34 (m, 1H, Pyridine); 8.70-8.78 (m, 2H, pyridine).

Stage C

Sodium salt of 1,1-dimethylethyl trans [[2-(carbamoylmethyl-carbamoyl)-4,5,6,8-tetrahydro-6-oxo-5-(sulphooxy)-4,7-methano-7H-pyrazolo[3,4-e][1,3]diazepin-8-yl]methyl]-carbamate By proceeding as indicated in Stage E of Example 1, the salt obtained in the previous stage (55 mg, 0.097 mmol), DOWEX 50WX8 resin (8 g) and 2N soda (30 mL), after deposition of the product in solution in water and lyophilization, produce the expected sodium salt (38 mg, 0.074 mmol, 77%) in the form of white lyophilizate.

MS ((ES(−)): m/z [M−H]$^-$=488)

$^1$H NMR (400 MHz, DMSO-d$_6$): δ (ppm)=1.40 (s, 9H, C(CH$_3$)$_3$); 3.32-3.40 (m, 4H, N—CH$_2$—CH—N and CH—CH$_2$—NHBoc), 3.78 (m, 2H, N—CH$_2$—CO—N), 4.40-4.50 (m, 1H, N—CH$_2$—CH—N), 4.75 (m, 1H, N—CH—CH$_2$—NHBoc), 7.10-7.20 (m, 2H, NH and NH), 8.19 (s, 1H, H pyrazole), 8.45 (m, 1H, NH).

Stage D

Sodium and trifluoroacetate salt of trans-8-(aminomethyl)-2-(carbamoylmethyl-carbamoyl)-4,8-dihydro-5-(sulphooxy)-4,7-methano-7H-pyrazolo[3,4-e][1,3]diazepin-6(5H)-one By proceeding as indicated in Stage F of Example 1, the sodium salt obtained in the previous stage (35 mg, 0.068 mmol), dichloromethane (3 mL), trifluoroacetic acid (1 mL) produce the expected sodium and trifluoroacetate salt (34 mg, 0.054 mmol, 80%) in the form of white lyophilizate.

MS (ES(+)): m/z [M+H]$^+$=390

EXAMPLE 8

Sodium and trifluoroacetate salt of trans 8-(aminomethyl)-2-(dimethylaminosulphamoyl)-4,8-dihydro-5-(sulphooxy)-4,7-methano-7H-pyrazolo[3,4-e][1,3]diazepin-6(5H)-one Stage A

1,1-dimethylethyl trans [[2-(dimethylaminosulphamoyl)-4,5,6,8-tetrahydro-6-oxo-5-(phenylmethoxy)-4,7-methano-7H-pyrazolo[3,4-e][1,3]diazepin-8-yl]methyl]-carbamate Under nitrogen, the derivative obtained in Stage B of Example 1 (200 mg, 0.500 mmol) is put into solution in anhydrous tetrahydrofuran (7 mL). At −5° C., 60% sodium hydride in oil (30 mg, 0.751 mmol) is added in one portion. After 15 minutes, dimethylsulphamoyl chloride (160 µL, 1.502 mmol) is added dropwise. The temperature of the mixture is progressively returned to ambient. After stirring for 3 hours, the medium is hydrolysed and extracted with dichloromethane (10 mL). The aqueous phase is extracted with dichloromethane (10 mL). The combined organic phases are washed with a saturated aqueous solution of sodium chloride, dried over sodium sulphate, concentrated under reduced pressure in order to produce, after chromatography on a silica column (eluent gradient CH$_2$Cl$_2$/MeOH 100/0 to 98/2), the expected derivative (98 mg, 0.193 mmol, 39%) in the form of a white powder.

MS (ES+) m/z [M+H]$^+$=507

$^1$H NMR (300 MHz, CDCl$_3$): δ (ppm)=1.43 (s, 9H, C(CH$_3$)$_3$), 2.91 (s, 6H, N(CH$_3$)$_2$), 3.09 (dd, 1H, N—CH$_2$—CH—N), 3.32-3.44, 3.49-3.59 (m, 2H, CH—CH$_2$—NHBoc), 3.75 (m, 1H, N—CH$_2$—CH—N), 3.96 (d, 1H, N—CH$_2$—CH—N), 4.63 (m, 1H, CH—CH$_2$—NHBoc), 4.95 (AB, 2H, CH$_2$-Ph), 5.12 (broad, 1H, NH), 7.36-7.55 (m, 5H, Ph), 7.78 (s, 1H, H pyrazole).

Stage B

Pyridinium salt of 1,1-dimethylethyl trans [[2-(dimethylaminosulphamoyl)-4,5,6,8-tetrahydro-6-oxo-5-(sulphooxy)-4,7-methano-7H-pyrazolo[3,4-e][1,3]diazepin-8-yl]methyl]-carbamate By proceeding as indicated in Stage D of Example 1, the derivative obtained in the previous stage (90 mg, 0.178 mmol), dimethylformamide (0.26 mL), dichloromethane (0.79 mL) and 10% palladium on carbon, 50% water-wet (57 mg, 0.027 mmol) produce the expected debenzylated intermediate.

The debenzylated intermediate, pyridine (0.59 mL) and pyridine/sulphur trioxide complex (57 mg, 0.356 mmol), after chromatography on a silica column (eluent gradient CH$_2$Cl$_2$/MeOH 100/0 to 80/20), produce the expected derivative (39 mg, 0.067 mmol, 38%).

MS (ES(−)): m/z [M−H]$^-$=495

$^1$H NMR (300 MHz, MeOH-d$_4$): δ (ppm)=1.46 (s, 9H, C(CH$_3$)$_3$), 2.91 (s, 6H, N(CH$_3$)$_2$), 3.30-3.59 (m, 5H, N—CH$_2$—CH—N, CH—CH$_2$—NHBoc, N—CH$_2$—CH—N), 4.60 (m, 1H, CH—CH$_2$—NHBoc), 4.92 (d, 1H, N—CH$_2$—CH—N), 8.04 (m, 2H, Py), 8.14 (s, 1H, H pyrazole), 8.57 (m, 1H, Py), 8.84 (m, 2H, Py).

Stage C

Sodium salt of 1,1-dimethylethyl trans [[2-(dimethylaminosulphamoyl)-4,5,6,8-tetrahydro-6-oxo-5-(sulphooxy)-4,7-methano-7H-pyrazolo[3,4-e][1,3]diazepin-8-yl]methyl]-carbamate By proceeding as indicated in Stage E of Example 1, the salt obtained in the previous stage (35 mg, 0.061 mmol) deposited in a minimum amount of methanol, DOWEX 50WX8 resin (9 g) and 2N soda (19 mL), after elution with water and lyophilization, produce the expected sodium salt (31 mg, 0.060 mmol, 100%) in the form of a pink powder MS (ES(−)): m/z [M−H]$^-$=495

$^1$H NMR (300 MHz, MeOH-d$_6$): δ (ppm)=1.46 (s, 9H, C(CH$_3$)$_3$), 2.90 (s, 6H, C(CH$_3$)$_2$), 3.30-3.53 (m, 5H, N—CH$_2$—CH—N, CH—CH$_2$—NHBoc, N—CH$_2$—CH—N), 4.59 (m, 1H, CH—CH$_2$—NHBoc), 4.92 (d, 1H, N—CH$_2$—CH—N), 8.14 (s, 1H, H pyrazole).

Stage D

Sodium and trifluoroacetate salt of trans [[8-(aminomethyl)-2-(dimethylaminosulphamoyl)-4,8-dihydro-5-(sulphooxy)-4,7-methano-7H-pyrazolo[3,4-e][1,3] diazepin-6(5H)-one By proceeding as indicated in Stage F of Example 1, the sodium salt obtained in the previous stage (30 mg, 0.058 mmol), dichloromethane (0.8 mL), trifluoroacetic acid (1.6 mL) in dichloromethane (1.6 mL) produce the expected sodium and trifluoroacetate salt (27 mg, 0.051 mmol, 88%) in the form of a beige solid.

MS (ES(−)): m/z [M−H]$^-$=396

$^1$H NMR (300 MHz, DMSO-d$_6$): δ(ppm)=2.86(s, 6H, C(CH$_3$)$_2$), 3.33-3.45 (m, 5H, N—CH$_2$—CH—N, CH—CH$_2$—NHBoc, N—CH$_2$—CH—N), 4.71 (m, 1H, CH—CH$_2$—NHBoc), 4.85 (d,1H, N—CH$_2$—CH—N), 8.10 (broad, 3H, NH$_3^+$) 8.34 (s, 1H, H pyrazole).

EXAMPLE 9

Sodium and trifluoroacetate salt of trans [[8-(aminomethyl)-1-(carbamimidoyl)-4,8-dihydro-6-oxo-5-(sulphooxy)-4,7-methano-7H-pyrazolo[3,4-e] [1,3]diazepin-6(5H)-one Stage A 1,1-dimethylethyl trans [[1-[tert-butoxycarbonylamino-(tert-butoxycarbonyl imino)-methyl]-4,5,6,8-tetrahydro-6-oxo-5-(phenylmethoxy)-4,7-methano-7H-pyrazolo[3,4-e][1,3]diazepin-8-yl]methyl]-carbamate and 1,1-dimethylethyl trans [[2-[tert-butoxycarbonylamino-(tert-butoxycarbonyl imino)-methyl]-4,5,6,8-tetrahydro-6-oxo-5-(phenylmethoxy)-4,7-methano-7H-pyrazolo[3,4-e][1,3]diazepin-8-yl]methyl]-carbamate Under nitrogen, the derivative obtained in Stage B of Example 1 (300 mg, 0.751 mmol) is put into solution in dichloromethane (1.25 mL). Triethylamine (523 μL, 3.76 mmol) and N,N'-di-(tert-butoxycarbonyl)thiourea (415 mg, 1.50 mmol) are added, followed by mercury chloride (408 mg, 1.50 mmol). After stirring for 20 hours at ambient temperature, triethylamine (261 μL, 1.88 mmol) and N,N'-di-(tert-butoxycarbonyl)thiourea (208 mg, 0.751 mmol) are added, followed by mercury chloride (204 mg, 0.751 mmol). After stirring for 44 hours at ambient temperature in total, the medium is filtered on a 0.45 μm membrane, rinsed with dichloromethane (10 mL) and the filtrate is concentrated under vacuum. The residue is subjected to chromatography on a silica column (eluent gradient CH$_2$Cl$_2$/ethyl acetate 100/0 to 85/15 by 5%) in order to produce the expected N1-substituted derivative (110 mg, 0.171 mmol, 23%) in the form of a beige solid, as well as the expected N2-substituted derivative (137 mg, 0.213 mmol, 28%) in the form of a beige solid.

N1-Substituted Derivative:
MS (ES+) m/z [M+H]$^+$=642
$^1$H NMR (400 MHz, CDCl$_3$): δ (ppm)=1.44 (s, 9H, C(CH$_3$)$_3$), 1.48 (s, 9H, C(CH$_3$)$_3$), 1.55 (s, 9H, C(CH$_3$)$_3$), 3.35 (m, 2H, N—CH$_2$—CH—N), 3.68 (m, 1H, CH—CH$_2$—NHBoc), 3.83 (m, 1H, CH—CH$_2$—NHBoc), 3.93 (d, 1H, N—CH$_2$—CH—N), 4.92 (AB, 2H, CH$_2$-Ph), 5.02 (m, 1H, CH—CH$_2$—NHBoc), 5.38 (broad, 1H, NH), 7.41-7.44 (multiplet, 5H, Ph), 7.48 (s, 1H, H pyrazole), 8.93 (broad, 1H, NH).

N2-Substituted Derivative:
MS (ES+) m/z [M+H]$^+$=642
$^1$H NMR (400 MHz, CDCl$_3$): δ (ppm)=1.48 (s, 9H, C(CH$_3$)$_3$), 1.56 (s, 18H, 2×C(CH$_3$)$_3$), 3.07 (d, 1H, N—CH$_2$—CH—N), 3.28 (m, 1H, CH—CH$_2$—NHBoc), 3.32 (dd, 1H, N—CH$_2$—CH—N), 3.86 (m, 1H, CH—CH$_2$—NHBoc), 3.90 (d, 1H, N—CH$_2$—CH—N), 4.62 (m, 1H, CH—CH$_2$—NBoc), 4.92 (AB, 2H, CH$_2$-Ph), 5.19 (broad, 1H, NH), 7.41-7.44 (multiplet, 5H, Ph), 8.18 (s, 1H, H pyrazole), 8.70 (broad, 1H, NH).

Stage B

Pyridinium salt of 1,1-dimethylethyl trans [[1-[tert-butoxycarbonylamino-(tert-butoxycarbonylimino)-methyl]-4,5,6,8-tetrahydro-6-oxo-5-(sulphooxy)-4,7-methano-7H-pyrazolo[3,4-e][1,3]diazepin-8-yl]methyl]-carbamate By proceeding as indicated in Stage D of Example 1, the N1-substituted derivative obtained in the previous stage (110 mg, 0.171 mmol), dimethylformamide (0.49 mL), dichloromethane (1.47 mL) and 10% palladium on carbon, 50% water-wet (55 mg, 0.026 mmol) produce the expected debenzylated intermediate.

The debenzylated intermediate, pyridine (0.8 mL) and pyridine/sulphur trioxide complex (55 mg, 0.343 mmol), after chromatography on a silica column (eluent gradient CH$_2$Cl$_2$/MeOH 100/0 to 85/15 by 5%) produce the expected derivative (19 mg, 0.026 mmol, 16%) in the form of a beige solid.

MS (ES(+)): m/z [M+H]$^+$=632
$^1$H NMR (400 MHz, MeOH-d$_4$): δ (ppm)=1.50, 1.59 (s, 27H, 3×C(CH$_3$)$_3$), 3.51-3.57 (m, 3H, N—CH$_2$—CH—N, CH—CH$_2$—NHBoc), 3.96 (dd, 1H, N—CH$_2$—CH—N), 4.92 (signal H2O+N—CH$_2$—CH—N), (dd, 1H, CH—CH$_2$—NHBoc), 7.83 (s, 1H, H pyrazole)

Stage C

Sodium and trifluoroacetate salt of trans-8-(aminomethyl)-1-(carbamimidoyl)-4,8-dihydro-5-(sulphooxy)-4,7-methano-7H-pyrazolo[3,4-e] [1,3] diazepin-6(5H)-one By proceeding as indicated in Stage E of Example 1, the salt obtained in the previous stage (19 mg, 0.027 mmol), DOWEX 50WX8 resin (2.3 g) and 2N soda (12 mL) produce the expected sodium salt (17 mg, 0.027 mmol, 100%).

By proceeding as indicated in Stage F of Example 1, the sodium salt (17 mg, 0.027 mmol), dichloromethane (0.5 mL), trifluoroacetic acid (1 mL) in dichloromethane (1 mL) produce the expected sodium and trifluoroacetate salt (10 mg, 0.014 mmol, 53%) in the form of a beige solid.

MS (ES+) m/z [M+H]$^+$=335
$^1$H NMR (400 MHz, D$_2$O) in the form of 2 conformers: δ (ppm)=3.40-3.50, 3.54-3.63 (m, 4H, N—CH$_2$—CH—N and CH—CH$_2$—NH$_3^+$), 4.82 (m, 1H, CH(B)—CH$_2$—NH$_3^+$), 4.93 (d, 1H, N—CH$_2$—CH(B)—N), 4.99 (d, 1H, N—CH$_2$—CH(A)—N), 5.26 (m, 1H, CH(A)-CH$_2$—NH$_3^+$), 7.74 (s, 1H, H(B) pyrazole), 8.00 (s, 1H, H(A) pyrazole)

EXAMPLE 10

Sodium and trifluoroacetate salt of trans 8-(aminoethyl)-2-(carbamimidoyl)-4,8-dihydro-5-(sulphooxy)-4,7-methano-7H-pyrazolo[3,4-e] [1,3]diazepin-6(5H)-one Stage A Pyridinium salt of 1,1-dimethylethyl trans [[2-[tert-butoxycarbonylamino-(tert-butoxycarbonylimino)-methyl]-4,5,6,8-tetrahydro-6-oxo-5-(sulphooxy)-4,7-methano-7H-pyrazolo[3,4-e][1,3]diazepin-8-yl]methyl]-carbamate By proceeding as indicated in Stage D of Example 1, the N2-substituted derivative obtained in Stage A of Example 9

(137 mg, 0.213 mmol), dimethylformamide (0.61 mL), dichloromethane (1.83 mL) and 10% palladium on carbon, 50% water-wet (55 mg) produce the expected debenzylated intermediate.

The debenzylated intermediate, pyridine (0.9 mL) and pyridine/sulphur trioxide complex (68 mg, 0.429 mmol), after chromatography on a silica column (eluent gradient $CH_2Cl_2$/MeOH 100/0 to 85/15 by 5%), produce the expected derivative (33 mg, 0.046 mmol, 22%) in the form of a beige solid.

MS (ES(−)): m/z [M−H]$^−$=630

$^1$H NMR (400 MHz, MeOH-d$_4$): δ (ppm)=1.50, 1.58 (s, 27H, C(CH$_3$)$_3$), 3.40-3.83 (m, 4H, N—CH$_2$—CH—N, CH—CH$_2$—NHBoc), 4.68 (dd, 1H, CH—CH$_2$—NHBoc), 5.00 (d, 1H, N—CH$_2$—CH—N), 7.50 (m, 2H, Py), 7.92 (m, 1H, Py), 8.37 (s, 1H, H pyrazole), 8.59 (m, 2H, Py)

Stage B

Sodium and trifluoroacetate salt of trans 8-(aminomethyl)-2-(carbamimidoyl)-4,8-dihydro-5-(sulphooxy)-4,7-methano-7H-pyrazolo[3,4-e] [1,3] diazepin-6(5H)-one By proceeding as indicated in Stage E of Example 1, the salt obtained in the previous stage (33 mg, 0.046 mmol), DOWEX 50WX8 resin (4 g) and 2N soda (20 mL) produce the expected sodium salt (30 mg, 0.046 mmol, 100%).

By proceeding as indicated in Stage F of Example 1, the sodium salt (30 mg, 0.046 mmol), dichloromethane (0.9 mL), trifluoroacetic acid (1.7 mL) in dichloromethane (1.7 mL) produce the expected sodium and trifluoroacetate salt (24 mg, 0.046 mmol, 75%) in the form of a beige solid.

MS (ES(+)): m/z [M+H]$^+$=335

$^1$H NMR (400 MHz, D$_2$O): δ(ppm) =3.42-3.53, 3.69-3.76 (m, 4H, N—CH$_2$—CH—N and CH—CH$_2$—NH$_3^+$), 4.90 (m, 1H, CH—CH$_2$—NH$_3^+$), 5.04 (d, 1H, N—CH$_2$—CH—N), 8.39 (s, 1H, H pyrazole)

Stage A 1,1-dimethylethyl trans [[2-(1-tert-butoxycarbonyl-piperidine-4-carbonyl)-4,5,6,8-tetrahydro-6-oxo-5-(phenylmethoxy)-4,7-methano-7H-pyrazolo[3,4-e][1,3]diazepin-8-yl]methyl]-carbamate N-boc-isonipecotic acid (0.137 g, 0.6 mmol) is put into solution in dimethylformamide (3 mL) in the presence of diisopropylethylamine (0.297 mL, 1.8 mmol) then O-(1H-benzotriazol-1-yl)-N,N,N',N'-tetramethyluronium tetrafluoroborate (0.211 g, 0.6 mmol) is added followed by the pyrazole obtained in Stage B of Example 1 (239 mg, 0.6 mmol) in solution in dimethylformamide (1 mL). Stirring is maintained at ambient temperature for 1 hour then the reaction mixture is hydrolysed with water (15 mL) and extracted with ethyl acetate (30 mL). The organic phase is washed 5 times with water (15 mL), dried over magnesium sulphate then concentrated under vacuum. The crude reaction product is subjected to chromatography on a silica column (eluent cyclohexane/ethyl acetate 80/20 then 70/30) in order to produce the expected derivative (0.219 g, 0.36 mmol, 60%) in the form of an oil.

MS (ES(+)): m/z [M+H]$^+$=611

$^1$H NMR (400 MHz, CDCl$_3$): δ (ppm)=1.47 (s, 9H, C(CH$_3$)$_3$), 1.48 (s, 9H, C(CH$_3$)$_3$), 1.56-1.97 (m, 4H, C(O)CH—CH$_2$—CH$_2$—N), 2.81-2.97 (m, 2H, CH$_2$—N(Boc)-CH$_2$), 3.09 (dd, 1H, N—CH$_2$—CH—N), 3.25-3.40 (m, 2H, N—CH$_2$—CH—N, C(O)CH(CH$_2$)—CH$_2$), 3.63 (m, 1H, CH$_2$—NHBoc), 3.89 (m, 1H, CH$_2$—NHBoc), 4.01 (d, 1H, N—CH$_2$—CH—N), 4.09-4.23 (m, 2H, CH$_2$—N(Boc)-CH$_1$), 4.63-4.72 (m, 1H, CH—CH$_2$—NHBoc), 4.95 (AB, 2H, CH$_2$-Ph), 5.11 (broad, 1H, NH), 7.32-7.50 (m, 5H, aromatic Hs), 7.44 (s, 1H, H pyrazole).

Stage B

Pyridinium salt of 1,1-dimethylethyl trans [[2-(1-tert-butoxycarbonyl-piperidine-4-carbonyl)-4,5,6,8-tetrahydro-6-oxo-5-(sulphooxy)-4,7-methano-7H-pyrazolo[3,4-e][1,3] diazepin-8-yl]methyl]-carbamate By proceeding as indicated in Stage D of Example 1, the derivative obtained in the previous Stage A (0.214 g, 0.35 mmol), an anhydrous dimethylformamide/CH$_2$Cl$_2$ mixture 1/3 (2 mL) and 10% palladium on carbon, 50% water-wet (111 mg) produce the expected debenzylated intermediate.

The debenzylated intermediate, pyridine (1 mL) and pyridine/sulphur trioxide complex (0.111 mg, 0.70 mmol), after chromatography on a silica column (eluent gradient CH$_2$Cl$_2$/MeOH 100/0 to 85/15) produce the expected derivative (0.061 g, 0.090 mmol, 34%) in amorphous form.

$^1$H NMR (400 MHz, MeOH-d$_4$): δ (ppm)=1.29 (s, 9H, C(CH$_3$)$_3$), 1.32 (s, 9H, C(CH$_3$)$_3$), 1.50 (m, 2H, C(O)CH—CH$_2$—CH$_2$), 1.80 (m, 2H, C(O)CH—CH$_2$—CH$_2$), 2.79 (m, 2H, CH$_2$—N(Boc)-CH$_2$), 3.20-3.46 (m, 4H, CH—CH$_2$—NHBoc, N—CH$_2$—CH—N), 3.62 (m, 1H, C(O)CH—CH$_2$), 3.95 (m, 2H, CH$_2$—N(Boc)-CH$_2$), 4.46 (m, 1H, CH—CH$_2$—NHBoc), 4.78 (d, 1H, N—CH$_2$—CH—N), 8.17 (s, 1H, H pyrazole).

Stage C

Sodium salt of 1,1-dimethylethyl trans [[2-(1-tert-butoxycarbonyl-piperidine-4-carbonyl)-4,5,6,8-tetrahydro-6-oxo-5-(sulphooxy)-4,7-methano-7H-pyrazolo[3,4-e][1,3]diazepin-8-yl]methyl]-carbamate By proceeding as indicated in Stage E of Example 1, the derivative obtained in the previous stage (61 mg, 0.09 mmol), DOWEX 50WX8 resin (9.4 g) and 2N soda (50 mL) produce the expected derivative (55 mg, 0.088 mmol, 100%) in amorphous form.

MS (ES(−)): m/z [M−H]$^−$=599

$^1$H NMR (400 MHz, DMSO-d$_6$): δ (ppm)=1.45 (s, 9H, C(CH$_3$)$_3$), 1.48 (s, 9H, C(CH$_3$)$_3$), 1.53 (m, 2H, C(O)CH—CH$_2$—CH$_2$), 1.87 (m, 2H, C(O)CH—CH$_2$—CH$_2$), 2.91 (m, 2H, CH$_2$—N(Boc)-CH$_2$), 3.25-3.44 (m, 4H, CH—CH$_2$—NHBoc, N—CH$_2$—CH—N), 3.63 (m, 1H, C(O)CH—CH$_2$), 3.92 (m, 2H, CH$_2$—N(Boc)-CH$_2$), 4.44 (m, 1H, CH—CH$_2$—NHBoc), 4.81 (d, 1H, N—CH$_2$—CH—N), 7.09 (broad, 1H, NH), 8.17 (s, 1H, H pyrazole).

Stage D

Sodium and trifluoroacetate salt of trans-8-(aminomethyl)-4,8-dihydro-2-(piperidine-4-carbonyl)-5-(sulphooxy)-4,7-methano-7H-pyrazolo[3,4-e][1,3]diazepin-6(5H)-one By proceeding as indicated in Stage F of Example 1, the sodium salt (55 mg, 0.088 mmol), dichloromethane (2.28 mL), trifluoroacetic acid (1.14 mL) in dichloromethane (1.14 mL) produce the expected sodium and trifluoroacetate salt (53 mg, 0.082 mmol, 93%) in yellow amorphous form.

MS (ES(−)): m/z [M−H]$^−$=398

¹H NMR (400 MHz, DMSO-d₆): δ (ppm)=1.66 (m, 2H, CH₂—NH—CH₂), 1.95 (m, 2H, CH₂—NH—CH₂), 2.44-2.62, 2.85-3.00 and 3.17-3.42 (m, 9H, CH—CH₂—NH₃⁺, N—CH₂—CH—N, C(O)CH(CH₂)—CH₂ and CH₂—NH—CH₂), 4.65 (dd, 1H, CH—CH₂—NH₃⁺), 4.77 (d, 1H, N—CH₂—CH—N), 7.78 (s, 1H, H pyrazole), 8.00 (broad, 5H, NH₃⁺, NH₂⁺).

EXAMPLE 12

Sodium and trifluoroacetate salt of trans 8-(aminomethyl)-2-(3-amino-3-carboxy-propyl)-4,8-dihydro-5-(sulphooxy)-4,7-methano-7H-pyrazolo[3,4-e][1,3]diazepin-6(5H)-one Stage A 1,1-dimethyl trans [[2-(3-tert-butoxycarbonyl-3-tert-butoxycarbonylamino-propyl)-4,5,6,8-tetrahydro-6-oxo-5-(phenylmethoxy)-4,7-methano-7H-pyrazolo[3,4-e][1,3]diazepin-8-yl]methyl]-carbamate The compound obtained in Stage B of Example 1 (200 mg, 0.50 mmol) is put into solution in anhydrous dimethylformamide (3 mL) in the presence of boc-L-glutamic acid 1-tert-butyl ester (159 mg, 0.525 mmol) and 1-hydroxybenzotriazole hydrate (85 mg, 0.63 mmol) then N-(3-dimethylaminopropyl)-N'-ethylcarbodiimide hydrochloride (101 mg, 0.525 mmol) is added after cooling down to 0° C. The reaction mixture is stirred at ambient temperature overnight. After dilution with ethyl acetate, the mixture is washed successively with a 10% aqueous solution of tartaric acid, a saturated aqueous solution of NaHCO₃, H₂O, then a saturated aqueous solution of sodium chloride. The organic phase is dried over sodium sulphate, filtered then concentrated under vacuum. The crude product thus obtained is purified by chromatography on silica (eluent CH₂Cl₂/AcOEt 90/10) in order to produce the expected product (92 mg, 0.134, 27%)
MS (ES+) m/z [M+H]⁺=685
Stage B Pyridinium salt of 1,1-dimethyl trans [[2-(3-tert-butoxycarbonyl-3-tert-butoxycarbonylamino-propyl)-4,5,6,8-tetrahydro-6-oxo-5-(sulphooxy)-4,7-methano-7H-pyrazolo[3,4-e][1,3]diazepin-8-yl]methyl]-carbamate By proceeding as indicated in Stage D of Example 1, the derivative obtained in the previous stage (92 mg, 0.13 mmol), an anhydrous dimethylformamide/CH₂Cl₂ mixture 1/3 (0.8 mL) and 10% palladium on carbon, 50% water-wet (43 mg) produce the expected debenzylated intermediate.

The debenzylated intermediate, pyridine (380 μL) and pyridine/sulphur trioxide complex (43 mg, 0.27 mmol), after chromatography on a silica column (eluent CH₂Cl₂/MeOH 90/10), produce the expected salt (28 mg, 0.037 mmol, 19%).
MS (ES+) m/z [M+H]⁺=675
¹H NMR (400 MHz, MeOH-d₄): δ(ppm)=1.52 (m, 27H, 3×C(CH₃)₃)₃), 2.05 (m, 2H, C(O)CH₂—CH₂—CH—(N)CO₂t-Bu), 2.25 (m, 2H, C(O)CH₂—CH₂—CH—(N)CO₂t-Bu), 3.50 (m, 4H, N—CH₂—CH—N and CH—CH₂—NHBoc), 4.11 (m, 1H, C(O)CH₂—CH₂—CH—(N)CO₂t-Bu), 4.62 (dd, 1H, CH—CH₂—NHBoc), 5.05 (d, 1H, N—CH₂—CH—N), 8.42 (s, 1H, H pyrazole).

Stage C

Sodium and trifluoroacetate salt of trans 8-(aminomethyl)-2-(3-amino-3-carboxy-propyl)-4,8-dihydro-5-(sulphooxy)-4,7-methano-7H-pyrazolo[3,4-e][1,3]diazepin-6(5H)-one By proceeding as indicated in Stage E of Example 1, the derivative obtained in the previous stage (28 mg, 0.04 mmol), DOWEX 50WX8 resin (3.5 g) and 2N soda (17.5 mL) produce the expected sodium salt.

By proceeding as indicated in Stage F of Example 1, the sodium salt (17 mg, 0.027 mmol), dichloromethane (0.86 mL), trifluoroacetic acid (0.86 mL) in dichloromethane (0.86 mL) produce the expected sodium and trifluoroacetate salt (27 mg, 0.049 mmol, 100%) in the form of a yellow gum.
MS (ES+) m/z [M−H]⁻=417
¹H NMR (400 MHz, MeOH-d₄): δ(ppm)=2.21-2.44 (m, 5H, C(O)CH₂—CH₂—CH—(N)CO₂t-Bu, C(O)CH₂—CH₂—CH—(N)CO₂t-Bu), 3.36-3.54 (m, 4H, N—CH₂—CH—N and CH—CH₂—NHBoc), 4.11 (m, 1H, C(O)CH₂—CH₂—CH—(N)CO₂t-Bu), 4.82 (dd, 1H, CH—CH₂—NHBoc), 4.98 (d, 1H, N—CH₂—CH—N), 7.79 (s, 1H, H pyrazole).

EXAMPLE 13

Sodium and trifluoroacetate salt of trans 8-(guanidino-methyl)-4,8-dihydro-5-(sulphooxy)-4,7-methano-7H-pyrazolo[3,4-e][1,3]diazepin-6(5H)-one Stage A bis-bis(1,1-dimethylethyl) trans [[[4,5,6,8-tetrahydro-6-oxo-5-(phenylmethoxy)-4,7-methano-7H-pyrazolo[3,4-e][1,3]diazepin-8-yl]methyl]-carbonimidoyl]carbamate Under nitrogen, the intermediate azide obtained in Stage B of Example 1 (1.5 g, 4.6 mmol) is put into solution in tetrahydrofuran (29 mL) then the solution is cooled down to 0° C. Trimethylphosphine (1M in tetrahydrofuran, 4.6 mL, 4.6 mmol) is added. The solution is stirred for 2 hours at ambient temperature, then 1,3-bis-(Boc)-2-methyl-2-thiopseudourea (1.34 g, 4.6 mmol) is added. After stirring overnight at ambient temperature, water (0.83 mL, 46 mmol) is added, then the mixture is kept for 16 hours at 5° C. The latter is concentrated to dryness, then purified by chromatography on a silica column (eluent cyclohexane/ethyl acetate, gradient from 80/20 to 0/100) in order to produce the expected product (560 mg, 1.03 mmol, 22%).
MS (ES(+)): m/z [M+H]⁺=542
¹H NMR (400 MHz, CDCl₃): δ (ppm)=1.48 (s, 9H, C(CH₃)₃), 1.54 (s, 9H, C(CH₃)₃), 3.10 (d, 1H, N—CH₂—CH—N), 3.36 (dd, 1H, N—CH₂—CH—N, 3.70-3.80 (m, 1H, CH—CH₂—NH—C=NBoc), 4.00 (d, 1H, N—CH₂—CH—N), 4.13-4.25 (m, 1H CH—CH₂—NH—C=NBoc), 4.68 (dd, 1H, CH—CH₂—NH—C=NBoc), 4.93 (AB, 2H, CH₂-Ph), 7.28-7.44 (m, 6H, H pyrazole+Ph), 9.38 (broad, 1H, NH), 11.35 (broad, 1H, NH).

Stage B bis-bis(1,1-dimethylethyl) trans [[[1-tert-butoxycarbamate-4,5,6,8-tetrahydro-6-oxo-5-(phenylmethoxy)-4,7-methano-7H-pyrazolo[3,4-e][1,3]diazepin-8-yl]methyl]-carbonimidoyl]carbamate Under nitrogen, the compound obtained in the previous stage (130 mg, 0.24 mmol) is put into solution in dichloromethane (12 mL). N,N-dimethylaminopyridine (15 mg, 0.12 mmol) is added, followed by di-tert-butyl dicarbonate (105 mg, 0.48 mmol). After stirring overnight at ambient temperature, the medium is hydrolysed with a 10% aqueous solution of tartaric acid (10 mL). After stirring for 10 minutes, the phases are separated, the aqueous phase is extracted with dichloromethane (10 mL). The organic phases are collected, washed with water then with a saturated NaCl solution, dried over $MgSO_4$ and concentrated to dryness. The crude product is purified on a silica column (eluent cyclohexane/ethyl acetate gradient of 80/20 to 0/100) in order to provide the expected product (100 mg, 0.16 mmol, 65%).

MS (ES(+)): m/z [M$^+$]=642

$^1$H NMR (400 MHz, CDCl$_3$): δ (ppm)=1.43 (s, 9H, C(CH$_3$)$_3$), 1.46 (s, 9H, C(CH$_3$)$_3$), 1.54 (s, 9H, C(CH$_3$)$_3$), 3.14-3.36 (m, 2H, N—CH$_2$—CH—N), 3.87-3.93 (m, 2H, CH—CH$_2$—NH—C=Nboc, N—CH$_2$—CH—N), 4.16 (m, 1H CH—CH$_2$—NH—C=NBoc), 4.68 (dd, 1H, CH—CH$_2$—NH—C=NBoc), 4.79 (d, 1H, CH$_2$-Ph), 4.93 (d, 1H, CH$_2$-Ph), 7.32-7.35 (m, 5H, Ph), 7.83 (s, 1H, H pyazole), 8.90 (broad, 1H, NH), 11.38 (broad, 1H, NH).

Stage C

Sodium and trifluoroacetate salt of trans-8-(guanidino-methyl)-4,8-dihydro-5-(sulphooxy)-4,7-methano-7H-pyrazolo[3,4-e][1,3]diazepin-6(5H)-one By proceeding as indicated in Stage D of Example 1, the derivative obtained in the previous stage (88 mg 0.14 mmol), an anhydrous dimethylformamide/CH$_2$Cl$_2$ mixture 1/3 (0.8 mL) and 10% palladium on carbon, 50% water-wet (44 mg) produce the expected debenzylated intermediate.

The debenzylated intermediate, pyridine (0.4 mL) and pyridine/sulphur trioxide complex (43 mg, 0.272 mmol), after chromatography on a silica column (eluent CH$_2$Cl$_2$/methanol, gradient of 100/0 to 80/20), produce the expected compound (55 mg, 0.077 mmol, 56%).

MS (ES(+)): m/z [M+H]$^+$=632

By proceeding as indicated in Stage E of Example 1, the salt obtained in the previous stage (50 mg, 0.07 mmol), DOWEX 50WX8 resin (3.5 g) and 2N soda (17.5 mL) produce the expected sodium salt (42 mg, 0.064 mmol, 91%) in the form of a white lyophilizate.

MS (ES(-)): m/z [M-H]$^-$=630

By proceeding as indicated in Stage F of Example 1, the sodium salt (42 mg, 0.064 mmol, 91%), dichloromethane (3 mL), trifluoroacetic acid (2 mL) in dichloromethane (2 mL) produce the expected sodium and trifluoroacetate salt (40 mg, 0.058 mmol, 95%) in the form of a beige powder.

MS (ES(-)): m/z [M-H]$^-$=330

$^1$H NMR (400 MHz, D$_2$O): δ (ppm)=3.43-3.70 (m, 5H, N—CH$_2$—CH—N, CH—CH$_2$—NH—C=Nboc, CH—CH$_2$—NH—C=NBoc), 4.92 (d, 1H, N—CH$_2$—CH—N), 7.73 (s, 1H, H pyrazole) $^{19}$F NMR (300 MHz, DMSO-d$_6$): δ (ppm)=-74.17 (s, CF3)

EXAMPLE 14

Sodium and trifluoroacetate salt of trans 8-(guanidino-methyl)-4,8-dihydro-1-methyl-5-(sulphooxy)-4,7-methano-7H-pyrazolo[3,4-e][1,3]diazepin-6(5H)-one Stage A 6-(1,1-dimethylethyl) and 7-methyl 4,7-dihydro-1-methyl-4-((phenylmethoxy)amino)-1H-pyrazolo[3,4-c]pyridine-6(5H), 7-dicarboxylate The 6-(1,1-dimethylethyl) and 7-methyl (4,7-dihydro-4-hydroxy-1-methyl-1H-pyrazolo[3,4-c]pyridine-6(5H), 7-dicarboxylate derivative, described in the Application WO 02/100860 (Stage C, Example 18) (10 g, 32.12 mmol) is suspended in dichloromethane (100 mL) at ambient temperature under nitrogen and under stirring. The suspension is dissolved after the addition of triethylamine (14.30 mL, 10.28 mmol). A solution of methane sulphonyl chloride (11.4 mL, 96.36 mmol) in dichloromethane (12 mL) is added dropwise to the reaction medium cooled down to −78° C. After stirring for 30 minutes, the alcohol is completely converted to mesylate.

A solution of 0-benzyl-hydroxylamine in dichloromethane is freshly prepared from O-benzylhydroxylamine hydrochloride (25.4 g, 160.6 mmol). The O-benzylhydroxylamine hydrochloride is dissolved in a mixture of dichloromethane (100 mL) and water (50 mL). A 2N soda solution (85 mL, 176.66 mmol) is added at 0° C. After contact for 10 minutes and settling, the organic phase is dried over magnesium sulphate for 45 minutes, then concentrated to half its volume. The addition of this solution to the mesylate prepared above is carried out at −78° C. dropwise over 1 hour. The reaction mixture is stirred while allowing the temperature to return progressively to ambient temperature. The medium is treated by the addition of water (200 mL) and diluted with dichloromethane (100 mL). After stirring and settling, the aqueous phase is extracted with dichloromethane. The organic phase is washed with a saturated NaCl solution (200 mL), dried, then concentrated to dryness in order to produce a white amorphous powder which, after chromatography, leads to the expected derivative (8.25 g, 21.2 mmol, 66%).

MS (ES(+)): m/z [M+H]$^+$=417

$^1$H NMR (400 MHz, CDCl$_3$): Description of one of the two diastereoisomers (in the form of 2 rotamers) δ (ppm)=1.43 (s, 9H, C(CH$_3$)$_3$), 3.15 (dd, 1H, N—CH$_2$—CH—N), 3.68/3.70 (s, 3H, CH$_3$), 3.84 (s, 3H, CH$_3$), 3.98 (m, 2H, N—CH$_2$—CH—N), 4.6-4.8 (multiplet, 3H, NH—O—CH$_2$-Ph and N—CH$_2$—CH—N), 5.40/5.8 (s, 1H, CH—CO$_2$Me), 7.22-7.31 (multiplet, 5H, Ph), 7.40 (s, 1H, H pyrazole)

Stage B

Methyl trans 1-methyl-6-oxo-5-(phenylmethoxy)-4,5,6,8-tetrahydro-4,7-methano-1H-pyrazolo[3,4-e][1,3]diazepine-8 (7H) carboxylate A 4N HCl/dioxane solution (400 mL) is poured onto a solution of the derivative obtained in the previous stage (21 g, 50.42 mmol) dissolved in dioxane (50 mL) at ambient temperature. The reaction mixture is stirred for 30 minutes. The residue is taken up under stirring in a mixture of water (100 mL) and ethyl acetate (500 mL). A 20% concentrated ammonia solution (42 mL) is added at 0° C. Stirring is continued for 30 minutes. After settling, the aqueous phase is reextracted with ethyl acetate (2×300 mL), the last extraction being carried out after saturation of the aqueous phase with NaCl. The organic phase is dried then concentrated. The deprotected piperidine intermediate is obtained in the form of a yellow oil (15.7 g, 49.4 mmol, 98%) which is taken up in acetonitrile (400 mL). Triethylamine (21 mL, 151.2 mmol), then diphosgene (3.04 mL, 25.2 mmol), poured dropwise over 30 minutes, are added to this mixture cooled down to 0° C. After stirring overnight at ambient temperature, the medium is concentrated then taken up in ethyl acetate (500 mL) and treated with a 10% tartaric acid solution (200 mL). The mixture is stirred and decanted. The organic phase is washed with a 10% tartaric acid solution (2×200 mL), with a saturated NaCl solution, then dried and concentrated under reduced pressure. The white product obtained (15.3 g, 44.0 mmol, 89%) is taken up in dichloromethane (150 mL). 18-Diazabicyclo[5.4.0]undec-7-ene (7.53 mL, 50.04 mmol) is added dropwise. The mixture is stirred for 2 hours, treated with water (200 mL), stirred and decanted. The organic phase is washed with water (2×200 mL), then with a saturated NaCl solution (1×200 mL), dried over $MgSO_4$, then concentrated to dryness, in order to produce the expected derivative (14.72 g, 37.4 mmol, 85%), in the form of a white solid.

MS (ES(+)): m/z $[M+H]^+$=343

$^1$H NMR (400 MHz, $CDCl_3$): δ (ppm)=3.25 (d, 1H, N—$CH_2$—CH—N), 3.45 (d, 1H, N—$CH_2$—CH—N), 3.80 (s, 3H, $CH_3$), 3.88 (s, 3H, $CH_3$), 3.9 (s, 1H, N—$CH_2$—CH—N), 4.7 (d, 1H, N—O—$CH_2$-Ph), 5.02 (d, 1H, N—O—$CH_2$-Ph), 5.22 (s, 1H, CH—$CO_2Me$), 7.39-7.43 (multiplet, 6H, H pyrazole+Ph)

Stage C trans 4,8-dihydro-8-(hydroxymethyl)-1-methyl-5-(phenylmethoxy)-4,7-methano-7H-pyrazolo[3,4-e][1,3]diazepin-6(5H)-one A solution of the urea obtained in the previous stage (5 g, 14.60 mmol) in an anhydrous tetrahydrofuran (150 mL)/methanol (50 mL) mixture, under nitrogen and under stirring, is cooled down to −10° C. Lithium borohydride (668 mg, 30.67 mmol) is added to the reaction medium. After stirring for 2 hours at −10° C., an additional 1.2 eq. of $LiBH_4$ is added. The reaction is treated while cold 2 hours later with a 10% $NaH_2PO_4$ solution. The tetrahydrofuran and the methanol are evaporated off under reduced pressure (200 mbar, 40° C.). The residual mixture is taken up in ethyl acetate (200 mL), stirred and decanted. The aqueous phase is reextracted with ethyl acetate (100 mL). The organic phase is dried over magnesium sulphate then concentrated to dryness. The light yellow powder obtained (6.6 g) is subjected to chromatography on silica (eluent-ethyl acetate) in order to produce the expected derivative (3.2 g, 10.18 mmol, 64%).

MS (ES(+)): m/z $[M^+]$=315

$^1$H NMR (400 MHz, DMSO-$d_6$): δ (ppm)=3.16 (dd, 1H, N—$CH_2$—CH—N), 3.48 (d, 1H, N—$CH_2$—CH—N), 3.71 (s, 3H, $CH_3$), 3.81-3.91 (multiplet, 2H, $CH_2OH$), 4.44 (m, 1H, N—$CH_2$—CH—N), 4.48 (m, 1H, CH—$CH_2OH$), 4.88 (m, 2H, N—O—$CH_2$-Ph), 5.20 (m, 1H, OH), 7.35-7.40 (multiplet, 6H, H pyrazole+Ph).

Stage D trans 4,8-dihydro-1-methyl-8-[(methylsulphonyl)oxymethyl]-5-(phenylmethoxy)-4,7-methano-7H-pyrazolo[3,4-e][1,3]diazepin-6(5H)-one The alcohol obtained in the previous stage (2.76 g, 8.78 mmol) is put into solution in dichloromethane (100 mL) at ambient temperature under nitrogen and under stirring. After cooling down to 0° C., triethylamine (1.83 mL, 13.17 mmol) then, dropwise, a solution of methanesulphonyl chloride (1.61 g, 14.05 mmol) in dichloromethane (100 mL) are added. The ice bath is removed at the end of the addition. After stirring for one hour at ambient temperature, the reaction medium is treated under stirring with a 10% $NaH_2PO_4$ solution (80 mL). The aqueous phase is reextracted with dichloromethane (50 mL). The organic phases are collected, dried, then concentrated under reduced pressure in order to produce the expected derivative (3.44 g, 8.78 mmol, quantitative yield).

MS (ES(+)): m/z $[M+H]^+$=393

$^1$H NMR (400 MHz, DMSO-$d_6$): δ (ppm)=3.23 (dd, 1H, N—$CH_2$—CH—N), 3.26 (s, 3H, $CH_3$), 3.45 (d, 1H, N—$CH_2$—CH—N), 3.76 (s, 3H, $CH_3$), 4.52 (m, 1H, N—$CH_2$—CH—N), 4.58 (dd, 1H, CH—$CH_2$—OMs), 4.66 (dd, 1H, CH—$CH_2$—OMs), 4.88 (m, 3H, CH—$CH_2$—OMs and N—O—$CH_2$-Ph), 7.35-7.45 (multiplet, 6H, H pyrazole+Ph)

Stage E

Trans 8-(azidomethyl)-4,8-dihydro-1-methyl-5-(phenylmethoxy)-4,7-methano-7H-pyrazolo[3,4-e][1,3]diazepin-6(5H)-one Sodium azide is added in one go (1.71 g, 26.3 mmol) to a solution of the mesylated derivative obtained in Stage D of Example 9 (3.44 g, 8.78 mmol) in dimethylformamide (70 mL) at ambient temperature under nitrogen and under stirring. The reaction medium is heated at 65° C. overnight, then treated with a 10% aqueous solution of $NaH_2PO_4$ (50 mL). The aqueous phase is extracted with dichloromethane (2×50 mL). The organic phase is dried then concentrated under reduced pressure to produce 3.96 g of the expected derivative (3 g, 878 mmol, 100%).

MS (ES(+)): m/z $[M^+]$32 340

$^1$H NMR (400 MHz, DMSO-$d_6$): δ (ppm)=3.20 (dd, 1H, N—$CH_2$—CH—N), 3.48 (d, 1H, N—$CH_2$—CH—N), 3.66 (dd, 1H, CH—$CH_2$—$N_3$), 3.72 (s, 3H, $CH_3$), 3.92 (dd, 1H, CH—$CH_2$—$N_3$), 4.50 (d, 1H, N—$CH_2$—CH—N), 4.76 (dd, 1H, CH—$CH_2$—$N_3$), 4.89 (m, 2H, N—O—$CH_2$-Ph), 7.35-7.45 (multiplet, 6H, H pyrazole+Ph)

Stage F bis-bis(1,1-dimethyl) trans [[[4,5,6,8-tetrahydro-1-methyl-6-oxo-5-(phenylmethoxy)-4,7-methano-7H-pyrazolo[3,4-e][1,3]diazepin-8-yl]methyl]-carbonimidoyl]carbamate Trimethylphosphine (1M in tetrahydrofuran, 0.46 mL, 0.46 mmol) is added dropwise to a solution of the derivative obtained in the previous stage (150 mg, 0.44 mmol) in tetrahydrofuran (2 mL) at 0° C. under nitrogen. After stirring for 3 hours at ambient temperature, 1,3-bis(tert-butoxycarbonyl)-2-methyl-2-thiopseudourea (141 mg, 0.48 mmol) is added to the reaction medium. After stirring overnight at ambient temperature, water (0.5 mL) is added and the medium is concentrated under reduced pressure in order to produce a pale yellow powder, which, after purification by chromatography on a silica column (eluent cyclohexane/ethyl acetate 5/5), leads to the expected product (152 mg, 0.273 mmol, 61%).

MS (ES(+)): m/z $[M+H]^+$=556, $[[M-(BOC)]^+]$=456, $[[M-(2BOC)]^+]$=356

$^1$H NMR (400 MHz, DMSO-d$_6$): δ (ppm)=1.40 (s, 9H, C(CH$_3$)$_3$), 1.50 (s, 9H, C(CH$_3$)$_3$), 3.20 (dd, 1H, N—$\overline{CH_2}$—CH—N), 3.35 (d, 1H, $\overline{N}$—CH$_2$—CH—N), 3.68 (m, $\overline{1H}$, CH—CH$_2$—NH), 3.79 (m, $\overline{1H}$, N—CH$_2$—CH—N), 3.86 (s, 3H,$\overline{CH_3}$), 4.50 (d, 1H, N—CH$_2$—$\overline{CH}$—N), 4.70 (m, 1H, CH—$\overline{CH_2}$—NH), 4.90 (m, 2H, CH$_2$-Ph), 7.35-7.41 (m, 6H, $\overline{Ph}$+H pyrazole), 8.68 (broad, 1H,$\overline{NH}$)

Stage G

Pyridinium salt of bis-bis(1,1-dimethyl) trans [[[4,5,6,8-tetrahydro-1-methyl-6-oxo-5-(sulphooxy)-4,7-methano-7H-pyrazolo[3,4-e][1,3]diazepin-8-yl]methyl]-carbonimidoyl]carbamate Under nitrogen, 10% palladium on carbon (100 mg) is added to a solution of the compound obtained in the previous stage (142 mg, 0.255 mmol) in methanol (5 mL). After three vacuum/nitrogen purges, the reaction medium is hydrogenated at atmospheric pressure over 3 hours. The methanol is concentrated under vacuum in order to produce the debenzylated intermediate.

The debenzylated intermediate is taken up in pyridine (1 mL) in the presence of pyridine/sulphur trioxide complex (82 mg, 0.511 mmol). After stirring overnight at ambient temperature, the medium is concentrated under vacuum. The crude reaction product is subjected to chromatography on a silica column (eluent gradient CH$_2$Cl$_2$/methanol 100/0 to 80/20), in order to produce the expected derivative (62 mg, 0.11 mmol, 45%).

MS (ES(+)): m/z [M+H]$^+$=546

$^1$H NMR (400 MHz, DMSO-d$_6$): δ (ppm)=1.42 (s, 9H, C(CH$_3$)$_3$), 1.51 (s, 9H, C(CH$_3$)$_3$), 3.28 (dd, 1H, N—$\overline{CH_2}$—CH—N), 3.36 (d, 1H,$\overline{N}$—CH$_2$—CH—N), 3.70 (m, $\overline{1H,}$CH—CH$_2$—NH), 3.80 (m, 1H,$\overline{CH}$—CH$_2$—NH), 3.87 (s, 3H, $\overline{CH_3}$), 4.68 (m, 2H, N—$\overline{CH_2}$—CH—N, CH—CH$_2$—$\overline{NH}$), 7.38 (s, 1H, H pyrazole), 8.90 (broad, 1H, $\overline{NH}$)

Stage H

Sodium salt of bis-bis(1,1-dimethyl)trans [[[4,5,6,8-tetrahydro-1-methyl-6-oxo-5-(sulphooxy)-4,7-methano-7H-pyrazolo[3,4-e][1,3]diazepin-8-yl]methyl]-carbonimidoyl]carbamate By proceeding as indicated in Stage E of Example 1, the derivative obtained in the previous stage (62 mg, 0.11 mmol), DOWEX 50WX8 resin (62 g) and 2N soda (300 mL) produce the expected derivative (57 mg, 0.11 mmol, 100%) in the form of a white amorphous powder.

MS (ES+) m/z [M+H]$^+$=546

$^1$H NMR (400 MHz, DMSO-d$_6$): δ (ppm)=1.42 (s, 9H, C(CH$_3$)$_3$), 1.51 (s, 9H, C(CH$_3$)$_3$), 3.27-3.34 (m, 2H, N—$\overline{CH_2}$—CH—N), 3.70 (m, $\overline{1H,}$CH—CH$_2$—NH), 3.80 (m, 1H, $\overline{CH}$—CH$_2$—NH), 3.87 (s, 3H, $\overline{CH_3}$), 4.68 (m, 2H, N—$\overline{CH_2}$—CH—N, CH—CH$_2$—$\overline{NH}$), 7.36 (s, 1H, H pyrazole), 8.78 ($\overline{broad, 1H, NH}$), 11.42 (broad, 1H, NH)

Stage I

Sodium and trifluoroacetate salt of trans 8-(guanidino-methyl)-4,8-dihydro-1-methyl-5-(sulphooxy)-4,7-methano-7H-pyrazolo[3,4-e][1,3]diazepin-6(5H)-one By proceeding as indicated in Stage F of Example 1, the sodium salt obtained in the previous stage (57 mg, 0.11 mmol), dichloromethane (7 mL), trifluoroacetic acid (3 mL) in dichloromethane (3 mL) produce the expected sodium and trifluoroacetate salt (56 mg, 0.11 mmol, 100%).

MS (ES(−)): m/z [M−H]$^-$=344

$^1$H NMR (400 MHz, DMSO-d$_6$): δ (ppm)=3.28 (m, 1H, N—CH$_2$—CH—N), 3.42 (m, 1H, N—CH$_2$—CH—N), 3.55 (m, $\overline{1H,}$CH—CH$_2$—NH), 3.69 (m, 1$\overline{H,}$ $\overline{CH}$—CH$_2$—NH), 3.78 (s, 3H, $\overline{CH_3)}$, 4.69-4.72 (m, 2H, N—$\overline{CH_2}$—CH—N, CH—CH$_2$—$\overline{NH)}$, 7.0-7.35 (m, 3H, NH$_3^+$), 7.40 (s, $\overline{1H}$, H pyrazole), 7.45 (broad, 1H, NH).

EXAMPLE 15

Sodium and trifluoroacetate salt of trans 8-(guanidino-methyl)-1-ethylcarbamoyl-4,8-dihydro-5-(sulphooxy)-4,7-methano-7H-pyrazolo[3,4-e][1,3]diazepin-6(5H)-one Stage A Bis-bis(1,1-dimethylethyl) trans [[[1-ethylcarbamoyl-4,5,6,8-tetrahydro-6-oxo-5-(phenylmethoxy)-4,7-methano-7H-pyrazolo[3,4-e][1,3]diazepin-8-yl]methyl]-carbonimidoyl]-carbamate and Bis-bis(1,1-dimethylethyl) trans [[[2-ethylcarbamoyl-4,5,6,8-tetrahydro-6-oxo-5-(phenylmethoxy)-4,7-methano-7H-pyrazolo[3,4-e][1,3]diazepin-8-yl]methyl]-carbonimidoyl]-carbamate The derivative obtained in Stage A of Example 13 (0.3 g, 0.55 mmol) is put into solution in an anhydrous acetonitrile/tetrahydrofuran mixture 8/2 (10 mL), under nitrogen. The solution is cooled down with an ice-water bath. Ethyl isocyanate (0.050 mL, 0.609 mmol) is then added dropwise. After stirring for a few minutes, the ice-water bath is removed. The reaction mixture is stirred at ambient temperature overnight. Water (0.3 mL, 0.017 mmol) is added, followed by ethanol (0.3 mL). The mixture is stirred for 30 minutes then concentrated under vacuum. The thick mixture obtained is taken up in the water (5 mL), then dichloromethane (10 mL) is added. After thorough stirring and settling, the aqueous phase is extracted with dichloromethane. The organic phases are combined, washed with a saturated NaCl solution, dried over magnesium sulphate and evaporated to dryness in order to produce a beige solid. This crude solid is purified by chromatography on a silica column (15 g, eluent CH$_2$Cl$_2$/AcOEt 100/0 then 97/3) in order to produce the N1-substituted compound (189 mg, 0.308 mmol, 55.7%) in the form of white solid and N2-substituted compound (71 mg, 0.116 mmol, 20.9%, N2) in the form of white solid.

N1-Substituted Derivative $^1$H NMR (400 MHz, CDCl$_3$): δ (ppm)=1.29 (t, 3H, N—CH$_2$—CH$_3$), 1.50 (s, 9H, C(CH$_3$)$_3$), 1.53 (s, 9H, C(CH$_3$)$_3$), 3.31-3.47 (m, 4H, N—CH$_2$—CH—N and N—CH$_2$—CH$_3$), 3.80-3.90 (m, 1H, CH—CH$_2$—NH—C=NBoc), 4.00 (d, 1H, N—CH$_2$—CH—N), 4.30-4.40 (m, 1H CH—CH$_2$—NH—C=NBoc), 4.87 (AB, 2H, N—O—CH$_2$-Ph), 5.10-5.17 (dd, 1H, CH—CH$_2$—NH—C=NBoc), 7.10 (broad, 1H, NH), 7.41-7.46 (m, 6H, H pyrazole+Ph), 8.8 (broad s, 1H, NH), 11.40 (s, 1H, NH).

N2-Substituted Derivative

MS (ES(+): m/z [M+H]$^+$=613

¹H NMR (400 MHz, CDCl₃): δ (ppm)=1.27 (t, 3H, N—CH₂—CH₃), 1.54 (s, 9H, C(CH₃)₃), 1.55 (s, 9H, C(CH₃)₃), 3.06 (AB, 1H, N—CH₂—CH—N), 3.40 (AB, 1H, N—CH₂—CH—N), 3.43-3.50 (m, 2H, N—CH₂—CH₃), 3.85-3.95 (m, 2H, CH—CH₂—NH—C=NBoc), 3.98 (d, 1H, N—CH₂—CH—N), 4.73 (dd, 1H, CH—CH₂—NH—C=NBoc), 4.87-5.05 (AB, 2H, N—O—CH₂-Ph), 7.20 (broad, 1H, NH), 7.42-7.45 (m, 5H 0-CH₂-Ph), 8.07 (s, 1H, H pyrazole), 8.9 (broad s, 1H, NH), 11.50 (s, 1H, NH).

Stage B

Pyridinium salt of bis-bis(1,1-dimethylethyl) trans [[[1-ethylcarbamoyl-4,5,6,8-tetrahydro-6-oxo-5-(sulphooxy)-4,7-methano-7H-pyrazolo[3,4-e][1,3] diazepin-8-yl]methyl]-carbonimidoyl]-carbamate By proceeding as indicated in Stage D of Example 1, the N1 derivative obtained in the previous stage (150 mg, 0.245 mmol), dimethylformamide (0.36 mL), dichloromethane (1.1 mL) and 10% palladium on carbon, 50% water-wet (78.2 mg, 0.037 mmol) produce the expected debenzylated intermediate.

The debenzylated intermediate, pyridine (0.74 mL) and pyridine/sulphur trioxide complex (78 mg, 0.245 mmol), after chromatography on a silica column (2 g, eluent gradient 100/0, 95/5, then 90/10) produce the expected derivative (78 mg, 0.114 mmol, 46.7%) in the form of white solid.

¹H NMR (400 MHz, MeOH-d₄): δ (ppm)=1.29 (t, 3H, N—CH₂—CH₃), 1.54 (s, 9H, C(CH₃)₃); 1.61 (s, 9H, C(CH₃)₃); 34.1-3.47 (m, 3H; N—CH₂—CH—N, and N—CH₂—CH₃); 3.60 (AB, 1H, N—CH₂—CH—N); 3.71 (d, 1H, N—CH₂—CH—N), 3.82-3.83 (dd, 1H, CH—CH₂—NH—C=NBoc), 4.40-4.44 (dd, 1H CH—CH₂—NH—C=NBoc), 5.01-5.04 (dd, 1H, CH—CH₂—NH—C=NBoc), 7.75 (s, 1H, H pyrazole).

Stage C

Sodium salt of bis-bis(1,1-dimethylethyl) trans [[[1-ethylcarbamoyl-4,5,6,8-tetrahydro-6-oxo-5-(sulphooxy)-4,7-methano-7H-pyrazolo[3,4-e][1,3]diazepin-8-yl]methyl]-carbonimidoyl]-carbamate By proceeding as indicated in Stage E of Example 1, the salt obtained in the previous stage (108 mg, 0.158 mmol) deposited in solution in water, DOWEX 50WX8 resin (23 g) and 2N soda (120 mL) produce the expected sodium salt (35 mg, 0.056 mmol, 35%) in the form of a white lyophilizate.

MS (ES(−)): m/z [M−H]⁻=601
¹H NMR (400 MHz, D₂O): δ (ppm)=1.12 (t, 3H, N—CH₂—CH₃), 1.37 (s, 9H, C(CH₃)₃), 1.43 (s, 9H, C(CH₃)₃), 3.30 (m, 2H, N—CH₂—CH₃), 3.52 (m, 1H, N—CH₂—CH—N), 3.70-3.76 (m, 2H, N—CH₂—CH—N and CH—CH₂—NH—C=NBoc), 4.27-4.33 (dd, 1H, CH—CH₂—NH—C=NBoc), 4.89 (s, 1H, N—CH₂—CH—N)), 4.96-5.10 (m, 1H, CH—CH₂—NH—C=NBoc), 7.70 (s, 1H, H pyrazole).

Stage D

Sodium and trifluoroacetate salt of trans 8-(guanidino-methyl)-1-ethylcarbamoyl-4,8-dihydro-5-(sulphooxy)-4,7-methano-7H-pyrazolo[3,4-e][1,3]diazepin-6(5H)-one By proceeding as indicated in Stage F of Example 1, the sodium salt obtained in the previous stage (35 mg, 0.055 mmol), dichloromethane (4 mL), trifluoroacetic acid (2 mL) produce the expected product (22 mg, 33 mmol, 61%) in the form of brown solid.

MS (ES+) m/z [M−H]⁻=401
¹H NMR (400 MHz, DMSO-d₆, 1 drop D₂O): δ (ppm)= 1.1-1.2 (m, 3H, N—CH₂—CH₃), 3.2-3.4 (m, 2H, N—CH₂—CH₃), 3.5-4.00 (m, 4H, CH—CH₂—NH—C=N and N—CH₂—CH—N), 4.63-4.70 (m, 1H, N—CH₂—CH—N), 4.8 (s, 1H, CH—CH₂—NH—C=N), 7.75/8.05 (s, H Pyrazole).

EXAMPLE 16

Sodium and trifluoroacetate salt of trans 8-(guanidino-methyl)-2-ethylcarbamoyl-4,8-dihydro-5-(sulphooxy)-4,7-methano-7H-pyrazolo[3,4-e][1,3] diazepin-6(5H)-one Stage A Pyridinium salt of bis-bis(1,1-dimethylethyl) trans [[[2-ethylcarbamoyl-4,5,6,8-tetrahydro-6-oxo-5-(sulphooxy)-4,7-methano-7H-pyrazolo[3,4-e][1,3] diazepin-8-yl]methyl]-carbonimidoyl]-carbamate By proceeding as indicated in Stage D of Example 1, the N2 derivative obtained in Stage A of Example 15 (80 mg, 0.130 mmol), dimethylformamide (0.19 mL), dichloromethane (0.76 mL) and 10% palladium on carbon, 50% water-wet (42 mg, 0.019 mmol) produce the expected debenzylated intermediate.

MS (ES+) m/z [M+H]⁺=523)
The debenzylated intermediate, pyridine (0.39 mL) and pyridine/sulphur trioxide complex (41.4 mg, 0.260 mmol), after chromatography on a silica column (2 g, eluent CH₂Cl₂/MeOH 100/0, 95/5, 90/10 then 85/15) produce the expected product (51 mg, 0.074 mmol, 57%) in the form of a beige solid.

MS (ES(+): m/z [M+H]⁺=603, m/z [M+H−(Boc)]⁺=503
¹H NMR (400 MHz, MeOH-d₄): δ (ppm)=1.26 (t, 3H, N—CH₂—CH₃), 1.54 (s, 9H, C(CH₃)₃), 1.61 (s, 9H, C(CH₃)₃), 3.43-3.47 (m, 2H, N—CH₂—CH₃), 3.52 (AB, 1H, N—CH₂—CH—N), 3.66 (AB, 1H, N—CH₂—CH—N), 3.82 (dd, 1H, CH—CH₂—NH—C=NBoc), 4.09 (dd, 1H, CH—CH₂—NH—C=NBoc), 4.77 (dd, 1H, N—CH₂—CH—N), 5.00 (dd, 1H, CH—CH₂—NH—C=NBoc), 8.31 (s, 1H, H pyrazole), Stage B Sodium salt of bis-bis(1,1-dimethylethyl) trans [[[2-ethylcarbamoyl-4,5,6,8-tetrahydro-6-oxo-5-(sulphooxy)-4,7-methano-7H-pyrazolo[3,4-e][1,3]diazepin-8-yl]methyl]-carbonimidoyl]-carbamate By proceeding as indicated in Stage E of Example 1, the salt obtained in the previous stage (49 mg, 0.072 mmol) deposited in solution in water, DOWEX 50WX8 resin (8 g) and 2N soda (50 mL) produce the expected sodium salt (18 mg, 0.029 mmol, 40%) in the form of a white lyophilizate.

MS (ES(−)): m/z [M−H]⁻=601) m/z [M−H−(Boc)]⁻=501
¹H NMR (400 MHz, D₂O): δ (ppm)=1.14 (t, 3H, N—CH₂—CH₃), 1.34 (s, 9H, C(CH₃)₃), 1.44 (s, 9H, C(CH₃)₃), 3.29-3.34 (m, 2H, N—CH₂—CH₃), 3.52-3.62 (m, 2H, CH—CH2—NH—C=NBoc), 3.72-3.77 (m, 1H, N—CH₂—CH—N), 3.87-3.92 (m, 1H, N—CH₂—CH—N), 4.75

(s, 1H, N—CH₂—CH—N), 5.00 (m, 1H, CH—CH₂—NH—C=NBoc), 8.22 (s, 1H, H pyrazole).
Stage C

Sodium and trifluoroacetate salt of trans 8-(guanidino-methyl)-2-ethylcarbamoyl-4,8-dihydro-5-(sulphooxy)-4,7-methano-7H-pyrazolo[3,4-e][1,3]diazepin-6(5H)-one By proceeding as indicated in Stage F of Example 1, the sodium salt obtained in the previous stage (18 mg, 0.028 mmol), dichloromethane (3 mL), trifluoroacetic acid (1.5 mL) produce the expected product. The suspension obtained by taking up the product in water is filtered in order to eliminate the insoluble fraction. The filtrate is frozen and lyophilized in order to produce the expected product (12 mg, 0.018 mmol, 64.5%) in the form of a slightly brown solid.

MS (ES(−)): m/z [M−H]⁻=401

¹H NMR (400 MHz, DMSO-d₆, 1 drop D₂O): δ (ppm)= 1.08-1.12 (m, 3H, N—CH₂—CH₃), 3.24-3.29 (m, 2H, N—CH₂—CH₃); 3.40 (broad, 2H, CH—CH2—NH—C=N); 3.63 (s, large, peak H₂O of the DMSO-d₆ and 2H of the N—CH₂—CH—N); 3.51-3.55 (t, 1H, N—CH₂—CH—N),), 4.84 (s, 1H, CH—CH₂—NH—C=N), 8.23 (s, 1H, H pyrazole).

EXAMPLE 17 trans 8-(guanidino-methyl)-2-carbamoyl-4,8-dihydro-5-(sulphooxy)-4,7-methano-7H-pyrazolo[3,4-e][1,3]diazepin-6(5H)-one Stage A

Bis-bis(1,1-dimethylethyl) trans [[[2-carbamoyl-4,5,6,8-tetrahydro-6-oxo-5-(phenylmethoxy)-4,7-methano-7H-pyrazolo[3,4-e][1,3]diazepin-8-yl]methyl]-carbonimidoyl]-carbamate The product obtained in Stage A of Example 13 (0.114 g, 0.21 mmol) is put into solution in an anhydrous acetonitrile/tetrahydrofuran mixture 40/60(3.5 mL), under nitrogen. The solution is cooled down with an ice-water bath. Then trimethylsilane isocyanate (0.030 mL, 0.21 mmol) is added dropwise. After stirring for 50 minutes, the ice-water bath is removed. The reaction mixture is stirred at ambient temperature overnight, then HPLC analysis still indicated the presence of 82% starting product. The reaction mixture is then cooled down again to 0° C. and trimethylsilane isocyanate (0.030 mL, 0.21 mmol) is added. A new addition of trimethylsilane isocyanate (0.030 mL, 0.21 mmol) is repeated after 30 hours, and the stirring is continued overnight. The reaction mixture is treated with the addition of water (1 mL) and methanol (1 mL). The mixture is stirred for 1 hour then evaporated to dryness. The solid obtained is taken up in 5 mL of water followed by stirring for 30 minutes, a white precipitate is observed. The latter is filtered out and dried under vacuum in order to produce 125 mg of crude product.

The reaction is implemented a second time on 150 mg (0.277 mmol) of substrate using 0.279 mL (1.94 mmol) of trimethylsilane isocyanate (added in 4 lots over 6 days), in order to produce 160 mg of crude product.

The two crude batches are combined and purified by chromatography on a silica column (10 g, eluent CH₂Cl₂/AcOEt 100/0, 95/05, 91/09 then 85/15). This makes it possible to isolate the expected N2-substituted compound (72 mg, 0.123 mmol, 25%) in the form of white solid.

¹H NMR (400 MHz, CDCl₃): δ (ppm)=1.50 (s, 9H, C(CH₃)₃), 1.53 (s, 9H, C(CH₃)₃), 3.00 (AB, 1H, N—CH₂—CH—N), 3.40 (AB, 1H, N—CH₂—CH—N), 3.78-3.85 (m, 1H, CH—CH₂—NH—C=NBoc), 3.99 (d, 1H, N—CH₂—CH—N), 4.00-408 (m, 1H, CH—CH₂—NH—C=NBoc), 4.74 (dd, 1H, CH—CH₂—NH—C=NBoc), 4.87-5.05 (AB, 2H, N—O—CH₂-Ph), 5.25 (broad, 1H, NH), 7.30 (s, 1H, NH), 7.42-7.45 (m, 5H 0-CH₂—Ph), 8.07 (s, 1H, H pyrazole), 9.00 (broad s, 1H, NH), 11.60 (s, 1H, NH).

Stage B

Pyridinium salt of bis-bis(1,1-dimethylethyl) trans-[[[2-carbamoyl-4,5,6,8-tetrahydro-6-oxo-5-(sulphooxy)-4,7-methano-7H-pyrazolo[3,4-e][1,3]diazepin-8-yl]methyl]-carbonimidoyl]-carbamate By proceeding as indicated in Stage D of Example 1, the derivative obtained in the previous stage (86 mg, 0.147 mmol), dimethylformamide (0.21 mL), dichloromethane (0.64 mL) and 10% palladium on carbon, 50% water-wet (47 mg, 0.022 mmol) produce the expected debenzylated intermediate.

The debenzylated intermediate, anhydrous pyridine (0.4 mL) and pyridine/sulphur trioxide complex (47 mg, 0.294 mmol, renewed after being left overnight), after chromatography on a silica column (2 g, eluent CH₂Cl₂/MeOH 100/0, 95/5, then 90/10) produce the expected product (57 mg, 0.087 mmol, 59%) in the form of white solid.

MS (ES(−)): m/z [M−H]⁻=573 m/z [M−H−(Boc)]⁻=473

¹H NMR (400 MHz, MeOH-d₄): δ (ppm)=1.50 (s, 9H, C(CH₃)₃); 1.62 (s, 9H, C(CH₃)₃); 3.49 (AB, 1H, N—CH₂—CH—N); 3.69 (AB, 1H, N—CH₂—CH—N); 3.98-4.02 (m, 2H, CH—CH₂—NH—C=NBoc); 4.79 (dd, 1H, N—CH₂—CH—N), 5.02 (d, 1H, CH—CH₂—NH—C=NBoc): 8.34 (s, 1H, H pyrazole).

Stage C

Sodium salt of bis-bis(1,1-dimethylethyl) trans [[[2-carbamoyl-4,5,6,8-tetrahydro-6-oxo-5-(sulphooxy)-4,7-methano-7H-pyrazolo[3,4-e][1,3] carbonimidoyl]-carbamate By proceeding as indicated in Stage E of Example 1, the salt obtained in the previous stage (57 mg, 0.087 mmol) deposited in solution in a minimum amount of water, DOWEX 50WX8 resin (10 g) and 2N soda (50 mL) produce the expected sodium salt (24 mg, 0.04 mmol, 46%) in the form of a white lyophilizate.

MS (ES(−)): m/z [M−H]⁻=573

¹H NMR (400 MHz, D₂O): δ (ppm)=1.36 (s, 9H, C(CH₃)₃), 1.43 (s, 9H, C(CH₃)₃), 3.56 (AB, 2H, N—CH₂—CH—N), 3.85 (d, 2H, CH—CH₂—NH—C=NBoc), 4.75 (broad, 1H, CH—CH₂—NH—C=NBoc), 4.95 (s, 1H, N—CH₂—CH—N), 8.25 (s, 1H, H pyrazole).

Stage D trans [[8-(guanidino-methyl)-2-carbamoyl-4,8-dihydro-5-(sulphooxy)-4,7-methano-7H-pyrazolo[3,4-e][1,3]diazepin-6(5H)-one By proceeding as indicated in Stage F of Example 1, the sodium salt obtained in the previous stage (24 mg, 0.04 mmol), dichloromethane (3 mL), trifluoroacetic acid (3 mL) produce the expected product. After evaporation under vacuum, the product is taken up in water. The suspension obtained is filtered. The solid is recovered and dried under vacuum overnight in order to produce the expected compound (4.9 mg, 0.013 mmol, 32.5%) in the form of beige solid.

MS (ES(−)): m/z [M−H]⁻=473

$^1$H NMR (400 MHz, DMSO-d$_6$, 1 drop D$_2$O): δ (ppm)= 3.40 (m, 2H, N—CH$_2$—CH—N), 3.60 (m, 2H, CH—CH$_2$—NH—C=N), 4.52 (broad, 1H, CH—CH$_2$—NH—C=N), 4.84 (s, 1H, N—CH$_2$—CH—N), 8.23 (s, 1H, H pyrazole).

EXAMPLE 18

Sodium and trifluoroacetate salt of trans 8-(aminomethyl)-4,8-dihydro-1-methyl-6-oxo-5-(carboxy-difluoro-methoxy)-4,7-methano-7H-pyrazolo[3,4-e][1,3] diazepin-6(5H)-one Stage A 1,1-dimethylethyl trans [[4,8-dihydro-1-methyl-6-oxo-5-(phenylmethoxy)-4,7-methano-7H-pyrazolo[3,4-e][1,3]diazepin-8-yl]methyl]-carbamate A molar solution of trimethylphosphine (3.4 mL, 3.4 mmol) is added dropwise to a solution of the azide obtained in Stage E of Example 14 (1.15 g, 3.39 mmol) in a mixture of toluene (5 mL) and tetrahydrofuran (5 mL) at ambient temperature under nitrogen and under stirring. After stirring for 3 hours, a solution of BOC—ON (0.92 g, 3.6 mmol) in tetrahydrofuran (10 mL) is added dropwise to the reaction medium cooled down to 0° C. Stirring is continued for 3 hours at ambient temperature. The reaction medium is treated with a 10% aqueous solution of NaHCO$_3$ (50 mL). The aqueous phase is extracted with ethyl acetate (50 mL). The organic phase is dried, then concentrated under reduced pressure to produce an oil (2.2 g). The crude product is subjected to chromatography on a silica column (eluent cyclohexane/ethyl acetate 5/5), in order to produce the expected product (0.62 g, 1.49 mmol, 70%).

MS (ES(+)): m/z [M⁺]=414

$^1$H NMR (400 MHz, CDCl$_3$): δ (ppm)=1.39 (s, 9H, C(CH$_3$)$_3$), 3.05 (dd, 1H, N—CH$_2$—CH—N), 3.19 (dd, 1H, CH—CH$_2$—NHBoc), 3.27 (dd, 1H, N—CH$_2$—CH—N), 3.72 (s, 3H, CH$_3$), 3.78 (m, 1H, CH—CH$_2$—NHBoc), 3.88 (d, 1H, N—CH$_2$—CH—N), 4.48 (dd, 1H, CHCH$_2$NHBoc), 4.79 (d, 1H, N—O—CH$_2$-Ph), 4.92 (d, 1H, N—O—CH$_2$-Ph), 5.18 (m, 1H, NH), 7.35 (s, 1H, H pyrazole), 7.37-7.48 (multiplet, 5H, Ph)

Stage B 1,1-dimethylethyl trans [[4,8-dihydro-1-methyl-6-oxo-5-(ethoxycarbonyl-difluoro-methoxy)-4,7-methano-7H-pyrazolo[3,4-e][1,3]diazepin-8-yl]methyl]-carbamate 10% palladium on carbon (70 mg) is added to a solution of the amine obtained in Stage A of Example 10 (300 mg, 0.72 mmol) in methanol (5 mL). The reaction medium is hydrogenated for 3 hours. The methanol is then evaporated off under reduced pressure in order to produce the debenzylated intermediate.

MS (ES(+)): m/z [M⁺]=324

The debenzylated intermediate (234 mg, 0.72 mmol) is taken up under nitrogen in anhydrous dimethylformamide (1.6 mL) in the presence of potassium carbonate (0.25 g, 1.81 mmol) and ethyl bromodifluoroacetate (0.373 mL, 2.89 mmol). The reaction is maintained under stirring at ambient temperature overnight. The reaction mixture is then filtered and rinsed with ethyl acetate. The filtrate is washed three times with water, the organic phase is dried over magnesium sulphate then concentrated under reduced pressure. The crude reaction product is subjected to chromatography on a silica column (eluent gradient CH$_2$Cl$_2$/methanol 100/0 to 95/5) in order to produce the expected derivative (185 mg, 0.42 mmol, 57%) in the form of an oil.

MS (ES(+)): m/z [M⁺]=446

$^1$H NMR (400 MHz, CDCl$_3$): δ (ppm)=1.37 (t, 3H, CH$_2$—CH$_3$), 1.60 (s, 9H, C(CH$_3$)$_3$), 3.24 (m, 1H, CH—CH$_2$—NHBoc), 3.33 (m, 1H, N—CH$_2$—CH—N), 3.53 (dd, 1H, N—CH$_2$—CH—N), 3.80-3.95 (m, 4H, CH$_3$ and CH—CH$_2$—NHBoc), 4.37 (m, 2H, CH$_2$—CH$_3$), 4.60-4.72 (m, 2H, N—CH$_2$—CH—N and CH—CH$_2$—NHBoc), 5.16 (broad, 1H, NH), 7.48 (s, 1H, H pyrazole)

Stage C 1,1-dimethylethyl trans [[4,8-dihydro-1-methyl-6-oxo-5-(carboxy-difluoro-methoxy)-4,7-methano-7H-pyrazolo[3,4-e][1,3]diazepin-8-yl]methyl]-carbamate Lithium hydroxide (0.017 g, 0.41 mmol) is added in two lots to a solution of the ester obtained in Stage B of Example 10 (0.181 g, 0.41 mmol) in a tetrahydrofuran/water mixture (7.38/2.48 mL) at 0° C. Stirring is continued at 0° C. for 1 hour 30 minutes. The reaction medium is treated with a 10% aqueous solution of tartaric acid and extracted twice with ethyl acetate. The organic phase is dried over magnesium sulphate, then concentrated under vacuum in order to produce the expected acid (110 mg, 0.32 mmol, 79%) in amorphous form.

MS (ES(+)): m/z [M⁺]=418

$^1$H NMR (400 MHz, MeOH-d$_4$): δ (ppm)=1.53 (s, 9H, C(CH$_3$)$_3$), 3.42-3.58 (m, 3H, CH—CH$_2$—NHBoc and N—CH$_2$—CH—N), 3.76 (dd, 1H, N—CH$_2$—CH—N), 3.90 (s, 3H, CH$_3$), 4.70-4.80 (m, 2H, N—CH$_2$—CH—N and CH—CH$_2$—NHBoc), 7.54 (s, 1H, H pyrazole).

Stage D

Sodium salt of 1,1-dimethylethyl trans [[4,8-dihydro-1-methyl-6-oxo-5-(carboxy-difluoro-methoxy)-4,7-methano-7H-pyrazolo[3,4-e][1,3]diazepin-8-yl]methyl]-carbamate Triethylamine (0.037 mL, 0.26 mmol) is added at 0° C. to a solution of the acid obtained in Stage C of Example 10 (0.110 mg, 0.26 mmol) in tetrahydrofuran (3 mL). Stirring is continued for 1 hour at 0° C. then the reaction mixture is concentrated under vacuum in order to produce the corresponding triethylamine salt (0.135 g, 0.26 mmol). A suspension of 16 g of DOWEX 50WX8 resin in a 2N soda solution (80 mL) is stirred for 1 hour, then poured onto a chromatography column. The column is eluted with demineralized water until a neutral pH is reached, then conditioned with a water/THF mixture 90/10. The triethylamine salt obtained previously (0.135 g, 0.26 mmol) is dissolved in a minimum amount of water, deposited on the column, then eluted with a water/THF mixture 90/10. The fractions containing the substrate are combined, frozen then lyophilized in order to produce the expected sodium salt (0.088 g, 0.20 mmol, 64%) in amorphous form.

MS (ES(−)): m/z [M⁻]=415

¹H NMR (400 MHz, MeOH-d₄): δ (ppm)=1.53 (s, 9H, C(CH₃)₃), 3.44-3.58 (m, 3H, CH—CH₂—NHBoc and N—CH₂—CH—N), 3.74 (dd, 1H, N—CH₂—CH—N), 3.90 (s, 3H, CH₃), 4.69-4.83 (m, 2H, N—CH₂—CH—N and CH—CH₂—NHBoc), 7.54 (s, 1H, H pyrazole).

Stage E

Sodium and trifluoroacetate salt of trans [[8-(aminomethyl)-4,8-dihydro-1-methyl-6-oxo-5-(carboxydifluoro-methoxy)-4,7-methano-7H-pyrazolo[3,4-e][1,3]diazepin-6(5H)-one A solution of trifluoroacetic acid (4.18 mL) in dichloromethane (4.18 mL) is poured dropwise onto a solution of the sodium salt obtained in Stage D of Example 10 (66 mg, 0.15 mmol) in dichloromethane (2.11 mL) under nitrogen and cooled down to 0° C. The reaction is maintained under stirring for 3 hours at 0° C. The mixture is evaporated to dryness, taken up in acetone, triturated and placed in a refrigerator overnight. The precipitate formed is filtered, rinsed with acetone and dried under vacuum in order to produce the expected sodium and trifluoroacetate salt (40 mg, 0.088 mmol, 59%) in the form of a light beige powder.

MS (ES(+)): m/z [M⁺]=318

¹H NMR (400 MHz, DMSO-d₆): δ (ppm)=3.27-3.60 (m, 4H, CH—CH₂—NH₃⁺ and N—CH₂—CH—N), 3.75 (s, 3H, CH₃), 4.71 (d, 1H, N—CH₂—CH—N), 4.82 (t, 1H, CH—CH₂—NH₃⁺), 7.44 (s, 1H, H pyrazole), 8.17 (broad, 3H, NH₃⁺).

EXAMPLE 19

Sodium and trifluoroacetate salt of trans 8-(aminomethyl)-2-amino-carbamoyl-4,8-dihydro-5-(sulphooxy)-4,7-methano-7H-pyrazolo[3,4-e][1,3]diazepin-6(5H)-one Stage A 1,1-dimethylethyl trans [2-(2-tert-butoxycarbonylamino-carbamoyl-4,5,6,8-tetrahydro-6-oxo-5-(phenylmethoxy)-4,7-methano-7H-pyrazolo[3,4-e][1,3]diazepin-8-yl]methyl]-carbamate By proceeding as indicated in Stage C of Example 1, the derivative obtained in Stage B of Example 1 (1 g, 2.5 mmol)), dichloromethane (131 mL), triethylamine (698 μL), diphosgene (453 μL) and N-Boc-hydrazine (1.158 g), after chromatography on a silica column (eluent gradient CH₂Cl₂/MeOH 100/0 to 95/5), produce the expected derivative (654 mg, 1.17 mmol, 47%).

MS (ES+) m/z [M+H]⁺=558

¹H NMR (400 MHz, DMSO-d₆): δ (ppm)=1.40 (s, 9H, (C(CH₃)₃)), 1.42 (s, 9H, (C(CH₃)₃)), 3.23-3.41 (m, 4H, N—CH₂—CH—N and NCH—CH₂—NHBOC), 4.39 (m, N—CH—CH₂—NHBOC), 4.62 (s, 1H, N—CH₂—CH—N), 4.91 (m, 2H, CH₂Ph), 7.13 (m, 1H, NH), 7.35-7.43 (m, 5H, Ph), 8.30 (s, 1H, pyrazole), 9.10 (s, 1H, NH), 10.22 (s, 1H, NH).

Stage B

Sodium salt of 1,1-dimethylethyl trans [2-(2-tert-butoxycarbonylamino-carbamoyl-4,5,6,8-tetrahydro-6-oxo-5-(sulphooxy)-4,7-methano-7H-pyrazolo[3,4-e][1,3]diazepin-8-yl]methyl]-carbamate By proceeding as indicated in Stage D of Example 1, the derivative obtained in the previous stage (654 mg, 1.17 mmol), dimethylformamide (3.3 mL), dichloromethane (10 mL) and 10% palladium on carbon, 50% water-wet (262 mg) produce the expected debenzylated intermediate.

The debenzylated intermediate, pyridine (4.5 mL) and pyridine/sulphur trioxide complex (373 mg), after chromatography on a silica column (eluent gradient CH₂Cl₂/MeOH 80/20), produce the expected derivative (43 mg) in the form of a white solid.

A suspension of 75 g of DOWEX 50WX8 resin in a 2N soda solution (375 mL) is stirred for 1 hour, then poured onto a chromatography column. The column is conditioned with demineralized water until a neutral pH is reached. The derivative obtained (431 mg) is dissolved in H₂O, deposited on the column, then eluted with H₂O. The fractions containing the substrate are combined, frozen and lyophilized in order to produce the expected sodium salt (362 mg, 0.63 mmol, 54%) in the form of a white powder.

MS (ES+) m/z [M–H]³¹ =546

¹H NMR (400 MHz, DMSO-d₆): δ (ppm)=1.42 (s, 18H, (C(CH₃)₃), 3.16-3.60 (m, 4H, N—CH₂—CH—N and N—CH—CH₂—NHBOC), 4.38 (t, 1H, N—CH—CH₂—NHBOC), 4.79 (s, 1H, N—CH₂—CH—N), 7.14 (m, 1H, NH), 8.23 (s, 1H, pyrazole), 9.17 (s, 1H, NH), 10.18 (s, 1H, NH).

Stage C

Sodium and trifluoroacetate salt of trans 8-(aminomethyl)-2-amino-carbamoyl-4,8-dihydro-5-(sulphooxy)-4,7-methano-7H-pyrazolo[3,4-e][1,3]diazepin-6(5H)-one The compound obtained in Stage B (362 mg, 0.635 mmol) is place in suspension in anhydrous dichloromethane (0.75 mL), under nitrogen. A trifluoroacetic acid/dichloromethane mixture 1/1 (0.944 mL) is then added dropwise then the reaction is continued at ambient temperature for three hours. After evaporation to dryness, the product is then taken up in water, frozen then lyophilized in order to produce the expected product in the form of white powder (363 mg, 0.607 mmol, 96%).

MS (ES+) m/z [M–H]⁻=346

¹H NMR (400 MHz, DMSO-d₆): δ (ppm)=3.07-4.19 (m, 4H, N—CH₂—CH—N and CH—CH₂—NH₂), 4.68 (dd, 1H, CH—CH₂—NH₃⁺), 4.70 (m, 1H, N—CH₂—CH—N), 8.15 (broad s, 3H, NH), 8.30 (s, 1H, H pyrazole).

Pharmaceutical Composition

A composition for injection was prepared containing:
Compound of Example 1 500 mg
Sterile aqueous excipient: q.s.f. 5 cm³

Pharmacological Study of the Compounds of the Invention

Activity in vitro, method of dilutions in liquid medium:

A series of tubes is prepared, into which the same quantity of sterile nutritive medium is distributed, increasing quantities of the product to be studied are distributed into each tube then each tube is seeded with a bacterial strain. After incubation for 24 hours in an oven at 37° C., growth inhibition is assessed by transillumination, which makes it possible to determine the minimum inhibitory concentrations (M.I.C.) expressed in μg/ml.

Tests are thus carried out with the products of Examples 1 to 19 in comparison with the products of Examples 11 of the Application WO 04/052891 and 18 of the Application WO 02/100860. The products of the present Application prove to be very active on *Pseudomonas aeruginosa*, which is not at all the case with the comparison products. The difference in activity on *Pseudomonas aeruginosa* between the products of the invention and the closest products of the prior art, depending on the products is situated at a level which can be up to 1000 times more active.

| Activity on *Pseudomonas aeruginosa* (1771 Wild-type strain) | |
|---|---|
| Molecules | MIC (µg/mL) 24 h (*P. aerug*, 1771) |
| Ex2 | 0.5 |
| Ex3 | 1 |
| Ex4 | 8 |
| Ex5 | 0.5 |
| Ex6 | 4 |
| Ex7 | 1 |
| Ex9 | 0.5 |
| Ex10 | 0.5 |
| Ex11 | 0.25 |
| Ex12 | 0.5 |
| Ex13 | 1 |
| Ex15 | >32 |
| Ex16 | 16 |
| Ex17 | 1 |
| Ex18 | 0.5 |
| Ex19 | 0.5 |
| Ex 11 Patent Application WO 04/052891 | >160 |
| Ex 18 Patent Application WO 02/100860 | >160 |

What is claimed is:

1. A compound of formula (I), or stereoisomers thereof:

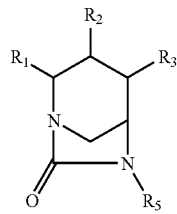

(I)

in which:

$R_1$ represents a hydrogen atom or a —$(CH_2)_m$—$NH_2$, —$(CH_2)_m$—$NH(C_1\text{-}C_6)$alk, —$(CH_2)_m$—$N[(C_1\text{-}C_6)alk]_2$, —$(CH_2)_m$—NH—$C(NH)NH_2$ or —$(CH_2)_m$—NH—CH=NH radical, in which m is 1 or 2;

$R_2$ and $R_3$ together form a pyrazolyl, substituted on a nitrogen atom by $R_4$;

$R_4$ represents a hydrogen atom, or a $(C_1\text{-}C_6)$alk radical or a chain of formula:

A represents a C=O, C=NH or $SO_2$ group;
R' represents a hydrogen atom or a carboxy group;
R" represents a hydrogen atom or an $NH_2$, $NH(C_1\text{-}C_6)$alk, $N[(C_1\text{-}C_6)alk]_2$, $CONH_2$, $CONH(C_1\text{-}C_6)$alk, $CON[(C_1\text{-}C_6)alk]_2$ group, a saturated heterocycle with 5 or 6 vertices containing 1 or 2 nitrogen atoms, or a saturated heterocycle with 5 or 6 vertices containing 1 or 2 nitrogen atoms and another heteroatom chosen from oxygen and sulphur, fixed to the chain by a nitrogen atom or by a carbon atom and optionally substituted by a $(C_1\text{-}C_6)$alk radical;
n, o and q independently represent 0 or 1 and p represents 0, 1, 2, 3, or 4;

$R_5$ represents an $OSO_3H$, $OCHFCO_2H$ or $OCF_2CO_2H$ group;

wherein:
$R_1$ is different from hydrogen, —$(CH_2)_m$—$NH_2$, —$(CH_2)_m$—$NH(C_1\text{-}C_6)$alk or —$(CH_2)_m$—$N[C_1\text{-}C_6)alk]_2$ when $R_4$ is hydrogen, —$(C_1\text{-}C_6)$alk, —$(C=O)_n$—$(CH_2)_{(0\text{-}5)}$—$NH_2$, —$(C=O)_n$—$(CH_2)_{(0\text{-}5)}$—$NH(C_1\text{-}C_6)$alk or —$(C=O)_n$—$(CH_2)_{(0\text{-}5)}$—$N[(C_1\text{-}C_6)alk]_2$ and $R_5$ is an $OSO_3H$ group, or when $R_4$ has all of the values of R" above except for the saturated heterocycle as defined above, and n, o, p and q cannot all be equal to 0 except when R" is hydrogen or a $CONH_2$, $CONH(C_1\text{-}C_6)$alk, $CON[(C_1\text{-}C_6)alk]_2$ group, or a saturated heterocycle;

and or wherein the compound is a free base or a pharmaceutically acceptable salt form.

2. A compound of formula (I) according to claim 1, wherein $R_1$ represents a —$(CH_2)_m$—$NH_2$ radical, in which m is 1.

3. A compound of formula (I) according to claim 1, wherein $R_1$ represents a —$(CH_2)_m$—NH—$C(NH)NH_2$ radical, in which m is 1.

4. The compound of formula (I) according to claim 1, wherein $R_4$ represents a chain of formula -$(A)_n$-$(NH)_o$—$(CH_2)_p$—$(CHR')_q$ R".

5. The compound of formula (I) according to claim 1, wherein $R_4$ represents a chain of formula —C(O)—NH—$(CH_2)_p$—$(CHR')_q$ R".

6. The compound of formula (I) according to claim 1, wherein $R_4$ represents a hydrogen atom or a $(C_1\text{-}C_6)$alk radical and $R_1$ represents a —$(CH_2)_m$—NH—$C(NH)NH_2$ or —$(CH_2)_m$—NH—CH=NH radical, in which m is 1.

7. The compound of formula (I) according to claim 1, selected from the group consisting of:

trans 8-(aminomethyl)-2-(2-amino-ethyl-carbamoyl)-4,8-dihydro-5-(sulphooxy)-4,7-methano-7H-pyrazolo[3,4-e] [1,3] diazepin-6(5H)-one, trans 8-(aminomethyl)-2-(4-piperazine-1-carbonyl)-4,8-dihydro-5-(sulphooxy)-4,7-methano-7H-pyrazolo[3,4-e] [1,3] diazepin-6(5H)-one, trans 8-(aminomethyl)-4,8-dihydro-2-(2-dimethylamino-ethyl-carbamoyl)-5-(sulphooxy)-4,7-methano-7H-pyrazolo[3,4-e] [1,3] diazepin-6(5H)-one, trans 8-(aminomethyl)-2-(3-amino-propyl-carbamoyl)-4,8-dihydro-5-(sulphooxy)-4,7-methano-7H-pyrazolo[3,4-e] [1,3] diazepin-6(5H)-one, trans 8-(aminomethyl)-2-(carbamoyl-methyl-carbamoyl)-4,8-dihydro-5-(sulphooxy)-4,7-methano-7H-pyrazolo [3,4-e] [1,3] diazepin-6(5H)-one, trans 8-(aminomethyl)-1-(carbamimidoyl)-4,8-dihydro-5-(sulphooxy)-4,7-methano-7H-pyrazolo[3,4-e] [1,3] diazepin-6(5H)-one, trans 8-(aminomethyl)-2-(carbamimidoyl)-4,8-dihydro-5-(sulphooxy)-4,7-methano-7H-pyrazolo[3,4-e] [1,3] diazepin-6(5H)-one, trans 8-(amino-methyl)-4,8-dihydro-2-(piperidine-4-carbonyl) -5-(sulphooxy)-4,7-methano-7H-pyrazolo[3,4-e] [1,3] diazepin-6(5H)-one, trans 8-(amino-methyl)-2-(3-amino-3-carboxy-propyl)-4,8-dihydro-5-(sulphooxy)-4,7-methano-7H-pyrazolo[3,4-e] [1,3] diazepin-6(5H)-one, trans 8-(guanidino-methyl)-4,8-dihydro-5-(sulphooxy)-4,7-methano-7H-pyrazolo[3,4-e] [1,3 9 diazepin-6(5H)-one, trans 8-(guanidino-methyl)-4,8-dihydro-1-methyl-5-(sulphooxy) -4,7-methano-7H-pyrazolo[3,4-e] [1,3] diazepin-6(5H)-one, trans 8-(guanidino-methyl)-2-carbamoyl-4,8-dihydro-(sulphooxy)-4,7-methano-7H-pyrazolo[3,4-e] [1,3] diazepin-6(5H)-one, trans 8-(amino-methyl)-4,8-dihydro-1-methyl-5-(carboxy-difluoro-methoxy)-4,7-methano-7H-pyrazolo[3,4-e] [1,3] diazepin-6(5H)-one, and trans 8-(amino-methyl)-2-(amino-carbamoyl)-4,8-dihydro-5-(sulphooxy)-4,7-methano-7H-pyrazolo[3,4-e] [1,3] diazepin-6(5H)-one, in a free base or a pharmaceutically acceptable salt form.

8. A medicament composition comprising an excipient and a compound according to claim 1.

9. A medicament composition comprising an excipient and a compound according to claim 7 or pharmaceutically acceptable salts thereof.

10. A pharmaceutical composition comprising an excipient and an active ingredient comprising a compound according to claim 1.

11. A pharmaceutical composition comprising a compound of formula (I), or stereoisomers thereof:

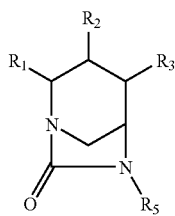

(I)

in which:

$R_1$ represents —$(CH_2)_m$—$NH_2$, in which m is 1 or 2;

$R_2$ and $R_3$ together form a pyrazolyl, substituted on a nitrogen atom by $R_4$;

$R_4$ represents a chain of formula:

$-(A)_n-(NH)_o-(CH_2)_p-(CHR')_q R''$

A represents a C=O, C=NH or $SO_2$ group;

R' represents a hydrogen atom or a carboxy group;

R" represents a hydrogen atom or an $NH_2$, $NH(C_1-C_6)$alk, $N[(C_1-C_6)alk]_2$ $CONH_2$, $CONH(C_1-C_6)$alk, $CON[(C_1-C_6)alk]_2$ group, or a saturated heterocycle with 5 or 6 vertices containing 1 or 2 nitrogen atoms or a saturated heterocycle with 5 or 6 vertices containing 1 or 2 nitrogen atoms and another heteroatom chosen from oxygen and sulphur, fixed to the chain by a nitrogen atom or by a carbon atom and optionally substituted by a $(C_1-C_6)$alk radical;

n, o and q independently represent 0 or 1 and p represents 0, 1, 2, 3 or 4; and $R_5$ represents an $OSO_3H$;

wherein the compound is a free base or a pharmaceutically acceptable salt form; and an excipient.

12. The pharmaceutical composition of claim 11, wherein $R_4$ represents a chain of formula: $-(A)_n-(NH)_o-(CH_2)_p-(CHR')_q R''$, wherein A represents a C=O group; R' represents a hydrogen atom; and R" represents an $NH_2$ group.

13. The pharmaceutical composition of claim 11, wherein the compound of formula (I) is trans 8-(aminomethyl)-2-(2-amino-ethyl-carbamoyl)-4,8-dihydro-5-(sulphooxy)-4,7-methano-7H-pyrazolo[3,4-e] [1,3] diazepin-6(5H)-one.

\* \* \* \* \*